(12) United States Patent
Tchistiakova et al.

(10) Patent No.: US 6,696,274 B2
(45) Date of Patent: Feb. 24, 2004

(54) LIGAND FOR ENHANCING ORAL AND CNS DELIVERY OF BIOLOGICAL AGENTS

(75) Inventors: Lioudmila Tchistiakova, Bothell, WA (US); Shengmin Li, Laval (CA); Grzegorz Pietrzynski, Montreal (CA); Valery Alakhov, Baie d'Urfe (CA)

(73) Assignee: Supratek Pharma, Inc. (CA)

( * ) Notice: Subject to any disclaimer, the term of this patent is extended or adjusted under 35 U.S.C. 154(b) by 0 days.

(21) Appl. No.: 09/848,537

(22) Filed: May 3, 2001

(65) Prior Publication Data

US 2002/0137684 A1 Sep. 26, 2002

Related U.S. Application Data

(60) Provisional application No. 60/201,981, filed on May 3, 2000.

(51) Int. Cl.[7] .................. C12P 21/06; A61K 38/04; A61K 38/00
(52) U.S. Cl. .............. 435/69.1; 530/327; 530/328; 530/332; 514/14; 514/15; 514/16
(58) Field of Search .................. 530/328, 327, 530/332; 514/14, 15, 16

(56) References Cited

FOREIGN PATENT DOCUMENTS

| | | |
|---|---|---|
| EP | 0599303 | 6/1994 |
| WO | WO 9856938 | 12/1998 |
| WO | WO 9922756 | 5/1999 |

OTHER PUBLICATIONS

Pardridge et al., "Chimeric Peptides As A Vehicle For Peptide Pharmaceutical Delivery Through The Blood–Brain Barrier," *Biochemical and Biophysical Research Communications*, 146(1):307–313 (Jul. 15, 1987).

Taylor et al., "Designing Stable Blood–Brain Barrier–Permeable Prosaptide Peptides For Treatment of Central Nervous System Neurodegeneration," *The Journal of Pharmacology and Experimental Therapeutics*, 293(2):403–409 (2000).

*Primary Examiner*—Brenda Brumback
*Assistant Examiner*—Billy D Chism
(74) *Attorney, Agent, or Firm*—Gibbons, Del Deo, Dolan, Griffinger & Vecchione

(57) ABSTRACT

Provided herein is a novel and useful Ligand comprising a peptide comprising an amino acid sequence of SEQ. ID. NO.:6, an analog, a derivative, or a variant thereof, which increases the absorption of biological agents across the blood brain barrier and the gastrointestinal barrier. As a result, a Ligand of the present invention increases the bioavailability of biological agents administered orally.

17 Claims, No Drawings

LIGAND FOR ENHANCING ORAL AND CNS DELIVERY OF BIOLOGICAL AGENTS

RELATED APPLICATIONS

The present application is based upon and claims the benefit of U.S. Provisional Application Serial No. 60/201,981 filed May 3, 2000.

FIELD OF THE INVENTION

The present invention generally relates to a composition comprising a peptide or analog or derivative thereof (Ligand) that is capable of enhancing oral and CNS bioavailability of therapeutics. More particularly, the present invention involves compositions comprised of a Ligand, or a complex of a Ligand with a carrier, which is associated with a biological agent.

BACKGROUND OF THE INVENTION

Optimized bioavailability of drugs administrated by oral route is one of the most important aims of the pharmaceutical industry during the development phase of a new product. Bioavailability represents both the quantity of a biological agent, i.e. the active component, absorbed from a pharmaceutical composition that is absorbed into blood and circulated, and the rate of this absorption. This implies that the molecule crosses one or several biological membranes before reaching the blood circulation. It has been generally considered that the physico-chemical properties of an orally administered drug determine its bioavailability. Among these parameters are the molecular weight (very low permeability is known for therapeutics with molecular weight more than 600 D), the pKa, and the lipophilicity as characterized by the octanol/water partition coefficient (Log D). The quantity of drug reaching the general circulation depends on the drug quantity absorbed by the intestinal epithelium, and drug solubility and stability in the gastrointestinal tract. Many classes of drugs present a large inter-individual variability in their absorption and/or a low bioavailability. Cytotoxic drugs used in anticancer therapy are a good example of drugs that are often poorly absorbed. Therapeutic peptides and proteins have also very low bioavailability by the oral route because they are easily metabolized in the stomach and intestine. In addition to problems related to degradation, the molecular weights of such peptides and proteins are typically too high to allow for significant transport across the gut wall into the circulatory system.

Since the advent of biotechnology, many protein therapeutics have been identified as having significant therapeutic benefits for many potentially serious diseases. Such diseases include cancer, heart disease, diseases of the central nervous system, diseases of the immune system, diseases of the blood and circulatory system, and many hormonally based diseases. Many of these medical disorders are chronic and require continuous administration of the required therapeutic.

A broad utilization of protein therapeutics, and many other hard to deliver therapeutics, depends on the ability of easily administering them to patients in a controllable and acceptable manner. The conventional route of therapy involving protein or peptide drugs is via parenteral administration (i.e., by injection), principally due to the lack of absorption of such drugs through the gastrointestinal tract. However, injections are painful and sometimes difficult to administer relative to other administration methods. Patient compliance is also an important consideration, since some of these drugs may require frequent administration to juvenile or geriatric patients. Clearly, oral administration is the most desirable method for administering such compounds to patients, who must take them for extended periods of time.

Although oral vaccination is more convenient, vaccines are generally given through injection. This is particularly true with killed or peptidic vaccines, because of their low absorption into the gastrointestinal tract. A problem with systemic immunization however, is that it may not effectively induce mucosal immune responses, for example, production of IgA, that are important as the first defense barrier to invaded microorganisms. For this reason, it would be beneficial to provide oral vaccination, if the problems of low intestinal absorption are resolved.

Recent efforts to deliver polypeptides and vaccines orally have focused on the use of absorption enhancers. This has led to the discovery that a suspension of sodium salicylate in an excess of oil can enhance the absorption of human growth hormone from the GI tract (EP publication 177,342; Moore et al., Internat. J. Phama. 34: 35 (1986)). While absorption is improved by this combination, the highest achievable bioavailability of the protein is only up to about 10–20% (with reference to intravenous administration), which is still quite low. As a result, larger amounts of proteins must be administered orally in order to provide the required therapeutic level of protein in the plasma. This is a particular problem with proteins and polypeptides that, even with the advent of biotechnology, are still of relatively limited availability, are complex chemical entities, and thus are very expensive. While the formulations discussed above have been found to improve absorption of proteins, polypeptides, and peptides in the colon somewhat, they also possess the inherent limitations and disadvantages explained above.

Accordingly, what is need is a novel and useful product that increases the absorption into the circulatory system from the gastrointestinal tract of a biological agent that is administered orally. What is also needed is a novel and useful product that increases absorption of a therapeutic agent across the Blood Brain Barrier (BBB), and thus increases the CNS bioavailability of a therapeutic agent.

The citation of any reference herein should not be construed as an admission that such reference is available as "Prior Art" to the instant application.

SUMMARY OF THE INVENTION

The present invention provides a polypeptide comprising at least one peptide or derivative thereof, wherein the polypeptide or derivative thereof is capable of crossing the small intestine and blood brain barrier. Such a polypeptide is herein referred to as Ligand.

In one embodiment, the present invention provides a peptide or derivative thereof that capable of is crossing the small intestine and blood brain barrier.

The polypeptide of the present invention comprising at least one peptide or derivative thereof, wherein the polypeptide or derivative thereof is capable of delivering biological agents across the small intestine and blood brain barrier.

A preferred peptide of the present invention provides the amino acid sequence of Arg-Val-Leu-Asp-Gly-Asp-Arg-Thr-Arg-Trp-Gly (SEQ. ID. NO.:4) wherein the peptide is capable of crossing the small intestine and blood brain barrier and delivering biological agents across the small intestine and blood brain barrier.

The present invention further provides a polypeptide, wherein the polypeptide or derivative thereof comprise the amino acid sequence of SEQ. ID. Nos.: 1, 2, 3, 4, 5, 6, or 7.

A preferred peptide, variant or derivative of peptide of the present invention has the sequence Arg-Val-X-Asp-X-Asp-X-Thr (SEQ. ID. NO.:7) (also abbreviated in single letter amino acid code as R V X D X D X T), where X is any amino acid).

Another embodiment of the present invention provides at least one peptide compound having the motif SEQ. ID. NO.:6:

$Y_1$-$Y_2$-X-$Y_3$-X-$Y_4$-X-$Y_5$, where $Y_1$ is positively charged amino acid such as Arg or Lys $Y_2$ is Val, Leu, Ile or Met $Y_3$ is negatively charged amino acid such as Glu or Asp $Y_4$ is negatively charged amino acid such as of Glu or Asp $Y_5$ is Thr or Ser X is any amino acid.

The polypeptide of the present invention further provides an extension at the carboxyl termini of polypeptide or derivative thereof wherein the carboxyl termini amino acid of the polypeptide or derivative thereof is bound to the C-terminal carboxyl group of the peptide. One embodiment of the present invention provides a pharmaceutical composition comprising the amino acid sequence of SEQ. ID. Nos.: 2, 3, or 5 wherein the carboxyl termini of alanine of said SEQ. ID. Nos.: 2, 3, or 5 is bound to carboxytetramethyl-rodamine.

The present invention also provides analogs of the polypeptide which can comprise in its molecular structure residues being derivatives of compounds other than amino acids, referenced herein as "peptide mimetics" or "peptido-mimetics". Other analogs of the peptide Ligand are compounds having changed topology of its chain, in particular nonlinear compounds which have chemical bonds that close cycle or cycles in the molecule and constraint its structure. Other analogs of the Ligand of the present invention include peptides with an altered sequence comprising another selection of L-α-amino acid residues, D-α-amino acid residues, non-α-amino acid residues.

The peptide Ligand of the present invention can be made by using well-known methods including recombinant methods and chemical synthesis. Recombinant methods of producing a peptide through the introduction of a vector including nucleic acid encoding the peptide into a suitable host cell is well known art, such as in described in Sambrook et al., Molecular Cloning: A Laboratory Manual, 2d Ed, Vols. 1 to 8, Cold Spring Harbor, N.Y. (1989), which is herein incorporated by reference. A linear amino acid sequence is synthesized, for example, by the solid phase peptide synthesis of Merrifield (Merrifield et al., *J. Am. Chem. Soc.*, 85:2149 (1964), which is incorporated herein by reference). Alternatively, a Ligand of the present invention can be synthesized using standard solution methods well known in the art (see, for example, Bodanszky, M., Principles of Peptide Synthesis (Springer-Verlag, 1984)), which is herein incorporated by reference). Newly synthesized Ligands of the present invention can be readily purified, for example, by high performance liquid chromatography (HPLC), and can be characterized using, for example, mass spectrometry or amino acid sequence analysis. Although a purity of greater than 95 percent for the synthesized peptide is preferred, lower purity is acceptable.

Therefore, in another embodiment, the polypeptide of the present invention provides that derivatives of SEQ. ID. NO.:4 comprise of oligopeptides, chemical derivatives or peptidomimetic that are capable of crossing the small intestine and blood brain barrier and delivering biological agents across the small intestine and blood brain barrier.

In another embodiment of the present invention, the Ligand is associated with a biological agent. Such an association can be achieved by chemical, genetic or physical linking of the Ligand and the biological agent, or by mixing the above components, or by their co-administration.

The peptide, derivative or peptidomimetic of this invention has one or more of the following activities:

The present invention provides a polypeptide comprising at least one peptide or derivative thereof, wherein the polypeptide or derivative thereof is capable of crossing the small intestine and blood brain barrier and delivering biological agents across the small intestine and blood brain barrier, wherein the polypeptide or derivative thereof which has at least about 20% of the biological activity of the polypeptide or derivative thereof of SEQ. I. NO.:4.

Still further, the present invention provides a polypeptide comprising at least one peptide or derivative thereof, wherein the polypeptide or derivative thereof has an oral therapeutic efficiency index of at least 0.0005, or a blood brain partitioning index of at least 1.

The biological activity of the present polypeptide can be measured by but is not limited to using in vitro bioassays comprising transport across Caco2 cells; transport across in vitro models of blood brain barrier, in vivo oral bioavailability analysis; or in vivo central nervous system bioavailability analysis.

The invention further includes a polypeptide comprising one or more Ligands in association with a carrier. In another embodiment of the invention, the Ligand is in association with a protein, virus, polymer or any other carrier to improve pharmacological properties of the Ligand to increase selectivity and efficacy the Ligand to deliver biological agents across blood brain barriers. The association of the ligand and the carrier can be achieved by chemical, genetic or physical linking of the Ligand and the carrier, or by mixing the above components, or by their co-administration.

In another embodiment of the invention, the Ligand associated with the carrier is further associated with a biological agent which is achieved by chemical, genetic or physical linking of the Ligand-carrier composition described in the previous embodiment of the invention and a biological agent. The invention further provides a pharmaceutical composition comprising one or more Ligands or their complex with a carrier in association with a biological agent.

In yet another embodiment of the invention, the Ligand is associated with a modified biological agent, which is achieved by chemical linking of the Ligand to the modified biological agent, such an association being a prodrug and revealing no activity of the biological agent. The active biological agent is released from such an associate upon action of chemical or enzymatic reaction in the body.

The present invention extends to a polypeptide comprising at least one Ligand of the present invention that is capable of enhancing oral and CNS bioavailability of therapeutic compounds. The invention further includes a polypeptide comprising one or more Ligands of the present invention in association with a carrier.

Moreover, the present invention extends to polypeptide for diagnostics and treatment of disease, where such diseases are associated with central nervous system (CNS) pathologies.

The invention is further directed to a polypeptide useful for diagnostics and treatment of CNS pathologies, comprising (a) any of the above peptides, variants or chemical derivatives including, but not limited to peptidomimetics; (b) a pharmaceutically acceptable carrier or excipient, either chemically conjugated or physically associated with the Ligand; and (c) at least one therapeutic agent.

The present invention further provides a polypeptide useful for diagnostics or treatment of CNS pathologies, comprising any of the above peptides, variants or chemical derivatives including a peptidomimetics conjugated chemically or genetically fused to a therapeutic agent.

Also provided is a method for inhibition of CNS pathologies in a subject having a disease or condition associated with undesired CNS pathologies comprising administering to the subject an effective amount of a pharmaceutical composition as described above.

The present invention also provides a method of treating a disease associated with CNS pathologies in s patient in need of such therapy comprising administering to said patient an effective amount of the pharmaceutical composition of the present invention and a pharmaceutically acceptable carrier.

These and other aspects of the present invention will be better appreciated by reference to the following drawings and Detailed Description.

DETAILED DESCRIPTION OF THE INVENTION

I. The Ligand

As explained above, the present invention provides a pharmaceutical composition comprising a Ligand that is capable of enhancing oral and CNS bioavailability of biological agents or formulations. The present invention also provides pharmaceutical compositions in which the Ligand is used as a targeting moiety to improve the delivery of a biological agent used to therapeutic or diagnostic purpose.

The preparation of a Ligand of the present invention is effected by means of one of the known organic chemical methods for peptide synthesis, or with the aid of recombinant DNA techniques.

II. Chemical Peptide Synthesis

The organic chemical methods for peptide synthesis are considered to include the coupling of amino acid residues by means of a condensation reaction, either in homogeneous phase or with the aid of a solid phase. The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester. The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.). A particularly useful method is the Castro type method using benzotriazole-1-yl-oxy-uronium, or -phoshponium esters, e.g. PyBOP (benzotriazole-1-yl-oxy-tris-pyrrolidino-phosphonium hexafluorophosphate) (Martinez, J. et al. (1988) *J. Med. Chem.* 28, 1874).

Preparation of a Ligand of the present invention using the "solid phase" is for instance described in *J. Amer. Chem. Soc.* 85, 2149 (1963) and *Int. J. Peptide Protein Res.* 35, 161–214 (1990). The coupling of the amino acids of a peptide to be prepared usually starts from the carboxyl end side. For this method, a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine function.

After synthesis of the desired amino acid sequence, detaching the peptide from the resin follows. For example, contacting the resin with hydrogen fluoride with trifluoromethanesulphonic acid, or with methanesulphonic acid dissolved in trifluoroacetic acid will detach the peptide from the resin. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

A particularly suitable solid phase is, for example, the Rink Amide resin (4-(2',4'-Dimethoxyphenyl-Fmoc-aminomethyl)-phenoxy-copolystrene-1% divinylbenzene resin), described by Rink (1987) *Tetrahedron Lett.*, 28, 3787. After synthesis, the peptide can be split from the solid phase under mild conditions using trifluoroacetic acid producing a carboxyamide derivative.

The reactive groups, which may not participate in the condensation reaction, are, as stated, effectively protected by groups, which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups that can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzenesulphonyl or p-toluenesulphonyl group. Other groups can also be used, such as substituted or unsubstituted aryl or arylalkyl groups, e.g., benzyl and triphenylmethyl, or groups such as orthonitrophenyl-sulphenyl and 2-benzoyl-1-methyl-vinyl. A particularly suitable a-amino-protective group is, for example, the base-sensitive 9-fluorenyl-methoxycarbonyl (Fmoc) group (Carpino & Han (1970) *J. Amer. Chem. Soc.* 92, 5748). A more extensive account of possible protecting groups can be found in The Peptides, Analysis, Synthesis, Biology, Vol.1–9 (Eds. Gross, Udenfriend and Meienhofer) 1979–1987 (Academic Press, Inc.).

It is necessary also to protect the β-amino group of lysine and advisable for the guanidine group of arginine. Customary protective groups in this connection are a Boc group for lysine and a Pmc, Pms, Mbs, or Mtr group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

III. Biosynthesis of the Ligand

Ligands of the present invention can be prepared by any technique, including by well-known recombinant methods. The above techniques are more fully described in laboratory manuals such as "Molecular Cloning: A Laboratory Manual", Second Edition by Sambrook et al., Cold Spring Harbor Press, 1989; "Current Protocols in Molecular Biology", Volumes I–III, Ausubel, R. M., ed., 1994; "Cell Biology: A Laboratory Handbook", Volumes I–III, J. E. Celis, ed., 1994; "Current Protocols in Immunology", Volumes I-III, Coligan, J. E., ed., 1994; "Oligonucleotide Synthesis", M. J. Gait ed., 1984; "Nucleic Acid Hybridization", B. D. Hames & S. J. Higgins eds., 1985; "Transcription And Translation", B. D. Hames & S. J. Higgins, eds., 1984; "Animal Cell Culture", R. I. Freshney, ed., 1986; "Immobilized Cells And Enzymes", IRL Press, 1986; B. Perbal, "A Practical Guide To Molecular Cloning", 1984.

DNA encoding a Ligand of the present invention can be prepared by a variety of methods known in the art. These methods include, but are not limited to, chemical synthesis by any of the methods described in Engels et al., Agnew. Chem. Int. Ed. EngI., 28: 716–734 (1989), the entire disclosure of which is incorporated herein by reference, such as the triester, phosphite, phosphoramidite and H-phosphonate methods. In one embodiment, codons preferred by the expression host cell are used in the design DNA that encodes a Ligand of the present invention. One example of a method of producing a Ligand using recombinant DNA techniques entails the steps of (1) synthetically generating DNA oligonucleotide that encodes a Ligand, appropriated linkers and restriction sites coding sequences (2) inserting the DNA into an appropriate vector such as an expression vector such that the DNA is operably linked with a promoter, (3) inserting the vector into a microorganism or other expression system capable of expressing the DNA, and (7) isolating the recombinantly Ligand.

Those skilled in the art will recognize that a Ligand of the present invention can also be produced in various cell systems, both prokaryotic and eukaryotic, all of which are within the scope of the present invention. The appropriate vectors include viral, bacterial and eukaryotic expression vectors. A nucleic acid molecule, such as DNA, is said to be "capable of expressing" a Ligand of the present invention if it contains nucleotide sequences that contain transcriptional and translational regulatory information and such sequences are "operably linked" to nucleotide sequences which encode the polypeptide. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

For example, the entire coding sequence of a DNA molecule that encodes a Ligand of the present invention may be combined with one or more of the following in an appropriate expression vector to allow for such expression: (1) an exogenous promoter sequence (2) a ribosome binding site (3) carrier protein (4) a polyadenylation signal (4) a secretion signal. Modifications can be made in the 5'-untranslated and 3'-untranslated sequences to improve expression in a prokaryotic or eukaryotic cell; or codons may be modified such that while they encode an identical amino acid, that codon may be a preferred codon in the chosen expression system. The use of such preferred codons is described in, for example, Grantham et al., Nuc. Acids Res., 9:43–74 (1981), and Lathe, J. MoL Biol., 183:1–12 (1985) hereby incorporated by reference herein in their entireties. Moreover, once cloned into an appropriate vector, the DNA can be altered in numerous ways as described to produce analogs, derivatives or variants of a peptide comprising an amino acid sequence of SEQ. ID. NO.:1, which are themselves Ligands of the present invention.

In another embodiment, a Ligand of the present invention can be expressed as a fusion protein in which the Ligand is fused at its N-terminus or its C-terminus, or at both termini, to one or more of peptide copies. In a particular embodiment, the fusion protein is specifically cleavable such that at least a substantial portion of Ligand can be proteolytically cleaved away from the fusion protein to yield the Ligand. Such a fusion protein can be designed with cleavage sites recognized by chemical or enzymatic proteases. In one embodiment, the fusion protein is designed with a unique cleavage site (or sites) for removal of the Ligand sequence, i.e. the fusion protein is designed such that a given protease (or proteases) cleaves away the Ligand but does not cleave at any site within the Ligand, and thus avoids fragmentation of the Ligand. In another embodiment, the cleavage site (or sites) at the fusion joint (or joints) is designed such that cleavage of the fusion protein with a given enzyme liberates the authentic, intact sequence of the Ligand from the remainder of the fusion protein sequence. The pTrcHisA vector (Invitrogen) and other like vectors can be used to obtain high-level, regulated transcription from the trc promoter for enhanced translation efficiency of a fusion protein comprising a Ligand of the present invention in *E. coli*. A Ligand of the present invention can also be expressed fused to an N-terminal nickel-binding poly-histidine tail for one-step purification using metal affinity resins. The enterokinase cleavage recognition site in the fusion protein allows for subsequent removal of the N-terminal histidine fusion protein from the purified Ligand. The Ligand fusion protein can be produced using appropriated carrier protein, for example, β-galactosidase, green fluorescent protein, luciferase, dehydrofolate reductase, thireodoxin, protein A Staphylococcus aureus and glutathione S-transferase. These examples are, of course, intended to be illustrative rather than limiting.

A Ligand of present invention can also be synthesized as a fusion protein with a virus coat protein, and expressed on the surface of virus particle, for example bacteriophage M13, T 7, T4 and lambda, gamma.gt10, gamma.gt11 and the like; adenovirus, retrovirus and pMAM-neo, pKRC and the like.

In general, prokaryote expression vectors contain replication and control sequences, which are derived from species compatible with the host cell. The vector ordinarily carries a replication site, as well as sequences that encode proteins capable of providing phenotypic selection in transformed cells. For example, vectors include pBR322 (ATCC No. 37,017), phGH107 (ATCC No. 40,011), pBO475, pS0132, pRITS, any vector in the pRIT20 or pRIT30 series (Nilsson and Abrahmsen, Meth. Enzymol., 185: 144–161 (1990)), pRIT2T, pKK233-2, pDR540, pPL-lambda, pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, pRIT5 (Pharmacia). Eukaryotic: pWLneo, pSV2cat, pOG44, pXT1, pSG (Stratagene) pSVK3, PBPV, pMSG, pSVL (Pharmacia) are suitable for expression in prokaryotic hosts. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). *Bacillus plasmids* include pC194, pC221, pT127, and the like. Such plasmids are disclosed by Gryczan (In: The Molecular Biology of the Bacilli, Academic Press, NY (1982), pp. 307–329). Suitable Streptomyces plasmids include p1J101 (Kendall et al., J. Bacteriol. 169:4177–4183 (1987)), and streptomyces bacteriophages such as .phi.C31 (Chater et al., In: Sixth International Symposium on Actinomycetales Biology, Akademiai Kaido, Budapest, Hungary (1986), pp.45–54). Pseudomonas plasmids are reviewed by John et al. (Rev. Infect. Dis. 8:693–704(1986)), and Izaki (*Jpn. J. Bacteriol.*33:729–742(1978)).

Prokaryotic host cells containing the expression vectors that encode for a Ligand of the present invention include *E. coli* K12 strain 294 (ATCC NO. 31446), *E coli* strain JM101 (Messing et al., *Nucl. Acid Res.*, 9: 309 (1981)), *E. coli* strain B, *E. coli* strain .sub..chi. 1776 (ATCC No. 31537), *E. coli* c600 (Appleyard, Genetics, 39: 440 (1954)), *E. coil* W3110 (F-, gamma-, prototrophic, ATCC No. 27325), *E. coil* strain 27C7 (W3110, tonA, phoA E15, (argF-lac)169, ptr3, degP41, ompT, kan.sup.r) (U.S. Pat. No. 5,288,931, ATCC No. 55,244), *Bacillus subtilis, Salmonella typhimurium, Serratia marcesans* and Pseudomonas species. For example, *E. coli* K12 strain MM 294 (ATCC No. 31,446) is particularly useful. Other microbial strains that may be used include *E. Coli* strains such as *E. coli* B and *E. coli* X1776 (ATCC No. 31,537). These examples are, of course, intended to be illustrative rather than limiting.

To express a Ligand of the present invention in a prokaryotic cell, it is necessary to operably link the Ligand-encoding DNA to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of *E. coli*, the aα-amylase (Ulmanen et al., *J. Bacteriol.* 162:176–182(1985)) and the ζ-28-specific promoters of *B. subtilis* (Gilman et al., *Gene Sequence* 32:11–20(1984)), the promoters of the bacteriophages of Bacillus (Gryczan, In: The Molecular Biology of the Bacilli, Academic Press, Inc., NY (1982)), and Streptomyces promoters (Ward et at., *Mol. Gen. Genet.* 203:468–478 (1986)). The most commonly used in recombinant DNA construction promoters include the P-lactamase (penicillinase) and lactose promoter systems (Chang et al., *Nature*, 375, 615 (1978); Itakura et al., *Science*, 198, 1056 (1977); Goeddel et al., *Nature*, 281, 544 (1979)) and a tryptophan (trp) promoter system (Goeddel et al., *Nucleis Acids Res.*, 8, 4057 (1980); EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell*, 20, 269 (1980)).

Proper expression in a prokaryotic cell also requires the presence of a ribosome binding site upstream of the gene sequence-encoding sequence. Such ribosome binding sites are disclosed, for example, by Gold et al. *Ann. Rev. Microbiol.* 35:365–404 (1981). The ribosome binding site and other sequences required for translation initiation are operably linked to the nucleic acid molecule encoding peptides of invention. Translation in bacterial system is initiated at the codon that encodes the first methionine. For this reason, it is preferable to include the ATG codon in peptide sequence and to ensure that the linkage between a promoter and a DNA sequence that encodes a peptide does not contain any intervening codons that are capable of encoding a methionine.

In addition to prokaryotes, eukaryotic organisms, such as yeasts, or cells derived from multicellular organisms can be used as host cells. Saccharomyces cerevisiae, or common baker's yeast, is the most commonly used among eukaryotic microorganisms, although a number of other strains are commonly available. For expression in Saccharomyces, the plasmid YRp7, for example (Stinchcomb et al., *Nature* 282, 39, 1979; Kingsman et al., *Gene* 7, 141 (1979); Tschemper et al., *Gene* 10:157 (1980.), is commonly used. This plasmid already contains the trpl gene that provides a selection marker for a mutant strain of yeast lacking the ability to grow in tryptophan, for example, ATCC No. 44,076 or PEP4-1 (Jones, *Genetics*, 85, 12 ,1977.). The presence of the trpl lesion as a characteristic of the yeast host cell genome then provides an effective environment for detecting transformation by growth in the absence of tryptophan. Suitable promoting sequences in yeast vectors include the promoters for 3- phosphoglycerate kinase (Hitzeman et al., *J. Biol. Chem.* 255, 2073 (1980)) or other glycolytic enzymes (Hess et al., *J. Adv. Enzyme Reg.* 7:149 (1968) Holland et al., *Biochemistry* 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459 (1988).

A Ligand of present invention can be produced in vertebrate host cells. The propagation of vertebrate cells in culture (tissue culture) has become a routine procedure in recent years (Tissue Culture, Academic Press, Kruse and Patterson, editors (1973). Examples of useful mammalian host cells include monkey kidney CVI line transformed by SV40 (COS-7, ATCC CRL 1651); human embryonic kidney line (293 or 293 cells subcloned for growth in suspension culture, Graham et al., *J. Gen Virol.*, 36: 59 (1977)); baby hamster kidney cells (BHK, ATCC CCL 10); Chinese hamster ovary cells/-DHFR (CHO, Urlaub and Chasin, *Proc. Natl. Acad. Sci. USA*, 77: 4216 (1980)); mouse Sertoli cells (TM4, Mather, Biol. Reprod., 23: 243–251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 (1982)); MRC 5 cells; FS4 cells; and a human hepatoma cell line (Hep G2). For expression in mammalian host cells, useful vectors include, but not limited vectors derived from SV40, vectors derived from cytomegalovirus such as the pRK vectors, including pRK5 and pRK7 (Suva et al., *Science*, 237: 893–896 (1987), EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

The production of a Ligand of the present invention expression of peptides of invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288(1982)); the TK promoter of Herpes virus (McKnight, *Cell* 31:355–365 (1982)); the SV40 early promoter (Benoist et al., *Nature* (London) 290:304–310(1981)); the yeast gal4 gene sequence promoter (Johnston et al., *Proc. Natl. Acad. Sci.* (*USA*) 79:6971–6975 (1982); Silver et al., *Proc. Natl. Acad. Sci.* (*USA*) 81:5951–5955 (1984)). An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. Satisfactory amounts of protein are produced by cell cultures; however, refinements, using a secondary coding sequence, serve to enhance production levels even further. One secondary coding sequence comprises dihydrofolate reductase (DHFR that is affected by an externally controlled parameter, such as methotrexate (MTX), thus permitting control of expression by control of the methotrexate concentration (Urlaub and Chasin, *Proc. Natl. Acad, Sci.* (*USA*) 77, 4216 (1980)).

Optionally, a Ligand of the present invention is operably linked to a secretory leader sequence resulting in secretion of the expression product by the host cell into the culture medium. Examples of secretory leader sequences include stII, ecotin, lamB, herpes GD, lpp, alkaline phsophatase, invertase, and alpha factor. Also suitable for use herein is the 36 amino acid leader sequence of protein A (Abrahmsen et al., *EMBO J.*, 4: 3901 (1985)).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, lipofection, calcium phosphate precipitation, direct microinjection, DEAE-dextran transfection, and the like. The most effective method for transfection of eukaryotic cell lines with plasmid DNA varies with the given cell type. After the introduction of the vector, recipient cells are grown in a selective medium, which selects for the growth of vector-containing cells. Expression of the cloned gene molecule(s) results in the production of a Ligand of the present invention. This can take place in the transformed cells or following the induction of these cells to differentiate (for example, by administration of bromodeoxyuracil to neuroblastoma cells or the like). A variety of incubation conditions can be used to form a Ligand of the present invention. The most preferred conditions are those that mimic physiological conditions.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell.

Transformation refers to introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook el al., Molecular Cloning (2nd ed.), Cold Spring Harbor Laboratory, New York (1989), is generally used for prokaryotes or other cells that contain substantial cell-wall barriers. Infection with Agrobacterium tumefaciens is used for transformation of certain plant cells, as described by Shaw et al., *Gene*, 23: 315 (1983) and WO 89/05859 published 29 June 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (*USA*), 76: 3829 (1979). However, other methods for introducing DNA into cells such as by nuclear injection, electroporation, or by protoplast fusion may also be used.

Host cells used to produce a Ligand of the present invention can be cultured in a variety of media as described generally in Sambrook et al. A wide variety of transcriptional and translational regulatory sequences may be employed, depending upon the nature of the host to control the expression. Transcriptional initiation regulatory signals may be selected which allow for repression or activation, so that expression of the gene sequences can be modulated. Of interest are regulatory signals, which are temperature-sensitive so that by varying the temperature, expression can be repressed or initiated, or are subject to chemical (such as metabolite) regulation.

In an intracellular expression system or periplasmic space secretion system, recombinantly produced Ligands of the present invention can be recovered from the culture cells by disrupting the host cell membrane/cell wall (e.g. by osmotic shock or solubilizing the host cell membrane in detergent). Alternatively, in an extracellular secretion system, a Ligand of the present invention that is recombinantly produced can be recovered from the culture medium. As a first step, the culture medium or lysate is centrifuged to remove any particulate cell debris. The membrane and soluble protein fractions are then separated. The Ligand can then be purified from the soluble protein fraction. If the Ligand is expressed as a membrane bound species, the membrane bound peptide can be recovered from the membrane fraction by solubilization with detergents. The crude peptide extract can then be further purified by suitable procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using IgG ligand immobilized on a matrix.

In vitro transcription/translation systems can also be employed to produce a Ligand of the present Invention using RNAs derived from a DNA molecule that encodes a peptide comprising an amino acid sequence of SEQ. ID. NO.: 1. Cell-free translation systems have been used in the biosynthesis of proteins and peptides, and have become a standard tool in molecular biology for protein production (In vitro transcription and translation protocols, Methods in Molecular Biology, 37 Edited by M. J. Tymms, 1995, Humana Press. Inc., Merrick, Translation of exogenous mRNAs in reticulocyte lysates, Meth. Enzymol. 101:38 (1983)). Kigawa, T. and Yokohama, S., "Continuous Cell-Free Protein Synthesis System for Coupled Transcription-Translation" Journal of Biochemistry 110:166–168 (1991), Baranov et al., "Gene expression in a cell-free system on the preparative scale" *Gene* 84:463466 (1989), Kawarasaki et al., "A long-lived batch reaction system of cell-free protein synthesis" *Analytical Biochemistry* 226:320–324 (1995)). Both eukaryotic and prokaryotic cell-free systems can be used for in vitro synthesis of a Ligand of the present invention. The rabbit reticulocyte (Pelham and Jackson, *Eur. J. Biochem.*, 67: 247–256 (1976)) and wheat germ lysate (Roberts and Paterson, *Proc. Natl. Acad. Sci.*, 70: 2330–2334 (1973)) methods are commonly used eukaryotic in vitro translation systems. The *E. coli* S30 extract method devised by Spirin, A. S. et al., "Continuous Cell-Free Translation System Capable of Producing Polypeptides in High Yield" *Science* 242 (4882): 1162–1164 (Nov. 25, 1988), Zubay, *Ann. Rev. Genet.*, 7: 267 (1973), and the fractionated method of Gold and Schweiger, *Meth. Enzymol.*, 20: 537 (1971) are widely used prokaryotic in vitro translation systems.

The expression unit for in vitro synthesis comprises a 5' untranslated region and may additionally comprise a 3' region. The 5' untranslated region of the expression unit contains a promoter or RNA polymerase binding sequence, a ribosome binding sequence, and a translation initiation signal. The 5' untranslated region ("head") may also contain convenient restriction sites and a translation enhancer or "Activator" sequence(s). The 3' region may contain convenient restriction sites and a 3' tail of a selected sequence. The expression unit may be chemically synthesized by protocols well known to those skilled in the art. Alternatively, these elements may be incorporated into one or more plasmids, amplified in microorganisms, purified by standard procedures, and cut into appropriate fragments with restriction enzymes before assembly into the expression unit.

The 5' untranslated region contains a promoter or RNA polymerase binding sequence, such as those for the T7, T3, or SP6 RNA polymerase. Positioned downstream of or within the promoter region is a DNA sequence, which codes for a ribosomal binding site. This ribosome binding site may be specific for prokaryotic ribosomal complexes (including ribosomal RNAs) if a prokaryotic translation procedure is used. However, a particular embodiment of the present invention utilizes a eukaryotic sequence and an in vitro eukaryotic translation system, such as the rabbit reticulocyte system (Krawetz et al., *Can. J. Biochem. Cell. Biol.* 61:274–286, 1983; Merrick, *Meth. Enzymol.* 101:38, 1983). A consensus translation initiation sequence, GCCGCCAC-CATGG, as well as other functionally related sequences have been established for vertebrate mRNAs (Kozak, *Nucleic Acids Res*, 15:8125–8148, 1987). This sequence or related sequences may be used in the DNA construction to direct protein synthesis in vitro. The ATG triplet in this initiation sequence is the translation initiation codon for methionine; in vitro protein synthesis is expected to begin at this point.

Between the promoter and translation initiation site, it may be desirable to place other known sequences, such as translation enhancer or "activator" sequences. For example, Jobling et al. (*Nucleic Acids Res*. 16:4483–4498 (1988)) showed that the untranslated "leader sequences" from tobacco mosaic virus "stimulated translation significantly" in SP6-generated mRNAs. They also reported that the 36-nucleotide 5' untranslated region of alfalfa mosaic virus RNA 4 increases the translational efficiency of barley amylase and human interleukin mRNAs (Jobling and Gehrke, *Nature* 325:622–625 (1987)). Black beetle virus (Nodavirus) RNA 2 (Friesen and Rueckert, *J. Virol.* 37:876–886 (1981)), tumip mosaic virus, and brome mosaic virus coat protein mnRNAs (Zagorski et al., *Biochimie* 65:127–133 (1983)) also translate at high efficiencies. In contrast, certain untranslated leaders severely reduce the expression of the SP6 RNAs (Jobling et al., ibid., (1988)).

In addition, a DNA molecule encoding a Ligand of the present invention may be incorporated into the in vitro expression unit. Within one embodiment, the expressed polypeptides contain both carrier polypeptide/peptide and Ligand amino acid sequences. The carrier peptide would be useful for quantifying the amount of fusion polypeptide and for purification (given that an antibody against the carrier polypeptide is available or can be produced). One example is the 11 amino acid Substance P, which can be attached as a fusion peptide to peptides of the invention. Anti-Substance P antibodies are commercially available for detecting and quantifying fusion proteins containing Substance P. Another example is the eight amino acid marker peptide, "Flag" (Hopp et al., *Bio/Technology* 6:1204–1210 (1988)). A preferable form of the carrier polypeptide is one, which may be cleaved from the novel polypeptide by simple chemical or enzymatic means.

IV. Ligands That are Analogs, Derivatives, or Variants of a Peptide Comprising an Amino Acid Sequence of SEQ. ID. NO.:1

As explained above, a Ligand having applications in a present invention comprises a peptide comprising an amino acid sequence of SEQ. ID. NO.:4, along with analogs, derivatives and variants of such a peptide. As used herein, the term "amino acid" and any reference to a specific amino acid is meant to include naturally occurring proteogenic amino acids as well as non-naturally occurring amino acids such as amino acid analogs. One of skill in the art would know that this definition includes, unless otherwise specifically indicated, naturally occurring proteogenic (D) or (L) amino acids, chemically modified amino acids, including amino acid analogs such as penicillamine (3-mercapto-D-valine), naturally occurring non-proteogenic amino acids such as norleucine and chemically synthesized compounds that have properties known in the art to be characteristic of an amino acid. As used herein, the term "proteogenic" indicates that the amino acid can be incorporated into a protein in a cell through well-known metabolic pathways.

The choice of including an (L)- or a (D)-amino acid into a Ligand of the present invention depends, in part, on the desired characteristics of the peptide. For example, the incorporation of one or more (D)-amino acids can confer increasing stability on the peptide in vitro or in vivo. The incorporation of one or more (D)-amino acids also can increase or decrease the binding activity of the peptide as determined, for example, using the binding assays described herein, or other methods well known in the art. In some cases, it is desirable to design a peptide that retains activity for a short period of time, for example, when designing a peptide to administer to a subject. In these cases, the incorporation of one or more (L)-amino acids in the peptide can allow endogenous peptidases in the subject to digest the peptide in vivo, thereby limiting a subject's exposure to an active peptide.

As used herein, the term "amino acid equivalent" refers to compounds, which depart from the structure of the naturally occurring amino acids, but which have substantially the structure of an amino acid, such that they can be substituted within a peptide, which retains is biological activity. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents.

As used herein, the term "peptide" is used in its broadest sense to refer to compounds containing amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. It is to be understood that limited modifications can be made to a peptide without destroying its biological function. Thus, modification of a peptide comprising an amino acid sequence of SEQ. ID. NO.:1 that does not completely destroy the activity of the peptide is a Ligand of the present invention. Such modifications can include, for example, additions, deletions, or substitutions of amino acids residues, substitutions with compounds that mimic amino acid structure or functions, as well as the addition of chemical moieties such as amino or acetyl groups. The modifications can be deliberate or accidental, and can be modifications of the composition or the structure.

Ligands of the present invention are also useful when they are maintained in a constrained secondary conformation. As used herein, the terms "constrained secondary structure," "stabilized" and "conformationally stabilized" indicate that the peptide bonds comprising the ligand are not able to rotate freely, but instead are maintained in a relatively fixed structure.

Various methods for constraining the secondary structure of a peptide are well known in the art and have applications in a Ligand of the present invention. For example, peptides such as those containing -Phe-Pro-Gly-Phe- sequence form β-turn, a well-known secondary structure. For example, a Ligand of the present invention can be stabilized by incorporating it into a sequence that forms a helix such as an alpha helix or a triple helix, according to methods described, for example, by Dedhar et al., *J. Cell. Biol.* 104:585 (1987); by Rhodes et al., *Biochein* 17:3442 (1978); and by Carbone et al., *J. Immunol* 138:1838 (1987), each of which is incorporated herein by reference. Additionally, a Ligand of the present invention can be incorporated into larger linear, cyclic or branched peptide, so long as its activity is retained.

A particular method for constraining the secondary structure of a newly synthesized linear peptide is to cyclize the peptide using any of various methods well known in the art. For example, a cyclized Ligand of the present invention can be prepared by forming a peptide bond between non-adjacent amino acid residues as described, for example, by Schiller et al., *Int. J. Pept. Prot. Res*. 25:171 (1985), which is incorporated herein by reference. Ligands can be synthesized on the Merrifield resin by assembling the linear peptide chain using $N^a$-Fmoc-amino acids with Boc and tertiary-butyl side chain protection. Following the release of the Ligand from the resin, a peptide bond can be formed between the amino and carboxyl termini of the Ligand.

A newly synthesized linear Ligand of the present invention can also be cyclized by the formation of a bond between reactive amino acid side chains. For example, a Ligand comprising a cysteine-pair can be synthesized and a disulfide bridge can be formed by oxidizing a dilute aqueous solution of the peptide with $K_3[Fe(CN)_6]$. Alternatively, a lactam such as an $\epsilon(\gamma$-glutamyl)-lysine bond can be formed between lysine and glutamic acid residues, a lysinonorleucine bond can be formed between lysine and leucine residues or a dityrosine bond can be formed between two tyrosine residues. Cyclic Ligands of the present invention can be constructed to contain, for example, four lysine residues, which can form the heterocyclic structure of desmosine (see, for example, Devlin, Textbook of Biochemistry 3rd ed. (1992), which is herein incorporated by reference).

Methods for forming these and other bonds are well known in the art and are based on well-known rules of chemical reactivity (Morrison and Boyd, Organic Chemistry, 6th Ed. (Prentice Hall, 1992), which is herein incorporated by reference).

V. Peptidoimetics

A ligand of the present invention can also comprise a peptidometic of a peptide comprising an amino acid sequence of SEQ. ID. NO.:. 1. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) *Adv. Drug Res*. 15:29; Veber and Freidinger (1985) TINS p.392; and Evans et al. (1987) *J. Med. Chem* 30:1229, which are incorporated herein by reference) and can be developed, for example, with the aid of computerized molecular modeling. Peptide mimetics that are structurally similar to a therapeutically useful peptide may be used to produce an equivalent therapeutic or prophylactic effect. Generally, peptidomimetics are structurally similar to a paradigm polypeptide (i.e., a polypeptide that has a biochemical property or pharmacological activity), such as a peptide comprising an amino acid sequence of SEQ. ID. NO.:.:1, but have one or more peptide linkages optionally replaced by a linkage selected from the group consisting of: —$CH_2$—NH—, —$CH_2$S—, —$CH_2$—$CH._2$—, —CH=CH— (cis and trans), —$COCH_2$ —, —CH(OH) $CH_2$ —, and —$CH_2$SO—, by methods known in the art and further described in the following references: Spatola, A. F. in "Chemistry and Biochemistry of Amino Acids, Peptides, and Proteins," B. Weinstein, eds., Marcel Dekker, N.Y., p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J. Pept Prot Res (1979) 14:177–185 (—$CH_2NH$—, —$CH_2$—$CH_2$—); Spatola, A. F. et al., Life Sci (1986) 38:1243–1249 (—$CH_2$—S); Hann. M. M., J. Chem Soc Perkin Trans I (1982) 307–314 (—CH=CH—, cis and trans); Almquist, R. G. et al., J Med Chem (1980) 23: 1392–1398 (—$COCH_2$—); Jennings-White, C. et al., Tetrahedron Lett (1982) 23:2533 (—$COCH_2$—); Szelke, M. et al., European Appln. EP 45665

(1982) CA.: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci (1982) 31:189–199 (—CH$_2$—S—); each of which is incorporated herein by reference. A particularly preferred nonpeptide linkage is —CH$_2$NH—. Such peptide mimetics may have significant advantages over a polypeptide, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) or cells to which the peptidomimetic interact to produce the therapeutic effect. Derivitization (e.g., labeling) of peptidomimetics should not substantially interfere with the desired biological or pharmacological activity of the peptidomimetic.

A variety of designs for peptide mimetics are possible. For example, cyclic peptides, in which the necessary conformation for binding is stabilized by nonpeptides, are specifically contemplated. U.S. Pat. No. 5,192,746 to Lobl, et al., U.S. Pat. No. 5,169,862 to Burke, Jr., et al, U.S. Pat. No. 5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred, et al., (J. Med. Chem. 37:3882 (1994)) describe nonpeptide antagonists that mimic the peptide sequence. Likewise, Ku, et al., (J. Med. Chem. 38:9 (1995)) give further elucidation of the synthesis of a series of such compounds.

Derivatives of a peptide comprising an amino acid sequence of SEQ. ID. NO.:1, which are Ligands of the present invention, can be produced using recombinant nucleic acid molecule techniques. Modifications to a specific peptide may be deliberate, as through site-directed mutagenesis and amino acid substitution during biosynthesis, or may be accidental such as through mutations in hosts, which produce the peptide. Peptides including derivatives can be obtained using standard mutagenesis techniques such as those described in Sambrook et al., Molecular Cloning, Cold Spring Harbor Laboratory Press (1989). For example, Chapter 15 of Sambrook describes procedures for site-directed mutagenesis of cloned DNA.

Derivatives of a peptide comprising an amino acid sequence of SEQ. ID. NO.:1 include, but certainly are not limited to modification of the peptide during or after translation, for example, by phosphorylation, glycosylation, crosslinking, acylation, proteolytic cleavage, linkage to a therapeutic protein, an antibody molecule, membrane molecule or other ligand (see Ferguson et al., 1988, Annu. Rev. Biochem. 57:285–320).

Specific types of genetically produced derivatives also include, but are not limited to amino acid alterations such as deletions, substitutions, additions, and amino acid modifications. A "deletion" refers to the absence of one or more amino acid residue(s) in the related peptide. An "addition" refers to the presence of one or more amino acid residue(s) in the related peptide. Additions and deletions to a peptide may be at the amino terminus, the carboxyl terminus, and/or internal, can be produced by mutating a DNA molecule that encodes a peptide comprising an amino acid sequence of SEQ. ID. NO.:1, and/or by peptide post-translation modification. Amino acid "modification" refers to the alteration of a naturally occurring amino acid to produce a non-naturally occurring amino acid. Analogs of a peptide comprising an amino acid sequence of SEQ. ID. NO.:1 with unnatural amino acids can be created by site-specific incorporation of unnatural amino acids into polypeptides during the biosynthesis, as described in Christopher J. Noren, Spencer J. Anthony-Cahill, Michael C. Griffith, Peter G. Schultz, Science, 244:182–188 (April 1989).

A "substitution" refers to the replacement of one or more amino acid residue(s) by another amino acid residue(s) in the peptide. Mutations can be made in a DNA molecule encoding a peptide comprising an amino acid sequence of SEQ. ID. NO.:1 such that a particular codon is changed to a different codon, which in turn codes for a different amino acid. Such a mutation is generally made by making the fewest nucleotide changes possible. A substitution mutation of this sort can be made to change an amino acid in the resulting peptide in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting peptide. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids. Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp). Derivatives can contain different combinations of alterations including more than one alteration and different types of alterations. "Derivatives" of a peptide comprising an amino acid sequence of SEQ. ID. NO.: 4 are functional equivalents having similar amino acid sequence and retaining, to some extent, the activities of a peptide comprising an amino acid sequence of SEQ. ID. NO.:4. By "functional equivalent" is meant the derivative has an activity that can be substituted for the activity of a peptide comprising an amino acid sequence of SEQ. ID. NO.:4. Preferred ftnctional equivalents retain the full level of transport efficacy through IB and BBB as measured by assays known to these skilled in the art, and/or described infra. Preferred ftunctional equivalents have activities that are within 1% to 10,000% of the activity of a peptide comprising an amino acid sequence of SEQ. ID.

NO.:4, more preferably between 10% and 1000%, and more preferably within 50% to 200%. Moreover, in a particular embodiment, derivatives have at least 50% sequence similarity, preferably 70%, more preferably 90%, and even more preferably 95% sequence similarity to a peptide comprising an amino acid sequence of SEQ. ID. NO.:4. "Sequence similarity" refers to "homology" observed between amino acid sequences in two different polypeptides, irrespective of polypeptide origin.

VI. Biological Agents

A variety of biological agents are suitable for use in the present invention. These include, without limitation, proteins, peptides (e.g., oligopeptides and polypeptides) including cytokines, hormones (such as insulin), and the like, recombinant soluble receptors, monoclonal antibodies, human growth hormones, tissue plasminogen activators, clotting factors, vaccines, colony stimulating factors, erythropoietins, enzymes, and dismultase.

Preferred classes of biological agents (including chemotherapeutic agents) include anti-neoplastic agents, antibacterial agents, antiparasitic agents, anti-fungal agents, CNS agents, immunomodulators and cytokines, toxins and neuropeptides. Biological agents for which target cells tend to develop resistance mechanisms are also preferred. Particularly preferred biological agents include anthracyclines such as doxorubicin, daunorubicin, epirubicin, idarubicin, mithoxanthrone or carminomycin, vinca alkaloids, mitomycin-type antibiotics, bleomycin-type antibiotics, azole antifungals such as fluconazole, polyene antifungals such as amphotericin B, taxane-related antineoplastic agents such as paclitaxel and immunomodulators such as tumor necrosis factor alpha (TNF-α), interferons and cytokines.

Preferred biological agents include, without limitation, additional antifungal agents such as amphotericin-B, flucytosine, ketoconazole, miconazole, itraconazole, griseofulvin, clotrimazole, econazole, terconazole, butoconazole, ciclopirox olamine, haloprogin, toinaftate, naftifine, nystatin, natamycin, undecylenic acid, benzoic acid, salicylic acid, propionic acid and caprylic acid. Such agents fturther include without limitation antiviral agents such as zidovudine, acyclovir, ganciclovir, vidarabine, idoxuridine, trifluridine, foxcarnet, amantadine, rimantadine and ribavirin. Such agents further include without limitation antibacterial agents such as penicillin-related compounds including 9-lactam antibiotics, broad spectrum penicillins and penicillinase-resistant penicillins (such as methicillin, nafcillin, oxacillin, cloxacillin, dicloxacillin, amoxicillin, ampicillin, ampicillin-sulbactam, azocillin, bacampicillin, carbenicillin, carbenicillin indanyl, cyclacillin, mezlocillin, penicillin G, penicillin V, piperacillin, ticarcillin, imipenem and aztreonam), cephalosporins (cephalosporins include first generation cephalosporins such as cephapirin, cefaxolin, cephalexin, cephradine and cefadroxil; second generation cephalosporins such as cefamandole, cefoxitin, cefaclor, cefuroxime, cefuroxime axetil, cefonicid, cefotetan and ceforanide; third generation cephalosporins such as cefotaxime, ceftizoxime, ceftriaxone, cefoperazone and ceftazidime), tetracyclines (such as demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Such agents further include agents active against protozoal infections such as chloroquine, diloxanide furoate, emetine or dehydroemetine, 8-hydroxyquinolines, metronidazole, quinacrine, melarsoprol, nifurtimox, pentamidine, sodium stibogluconate and suramin.

A variety of central nervous system biological agents are suitable for use in the present invention. These include neuroleptics such as the phenothiazines (such as compazine, thorazine, promazine, chlorpromazine, acepromazine, aminopromazine, perazine, prochlorperazine, trifluoperazine, and thioproperazine), rauwolfia alkaloids (such as reserpine and deserpine), thioxanthenes (such as chlorprothixene and tiotixene), butyrophenones (such as haloperidol, moperone, trifluoperidol, timiperone, and droperidol), diphenylbutylpiperidines (such as pimozide), and benzamides (such as sulpiride and tiapride); tranquilizers such as glycerol derivatives(such as mephenesin and methocarbamol), propanediols (such as meprobamate), diphenylmethane derivatives (such as orphenadrine, benzotrapine, and hydroxyzine), and benzodiazepines(such as chlordiazepoxide and diazpam); hypnotics (such as zolpdem and butoctamide); 9-blockers (such as propranolol, acebutonol, metoprolol, and pindolol); antidepressants such as dibenzazepines (such as imipramine), dibenzocycloheptenes (such as amitriptyline), and the tetracyclics (such as mianserine); MAO inhibitors (such as phenelzine, iproniazide,and selegeline); psychostimulants such as phenylethylamine derivatives (such as amphetamines, dexamphetamines, fenproporex, phentermine, amfepramone, and pemline) and dimethylaminoethanols (such as clofenciclan, cyprodenate, aminorex, and mazindol); GABA-minmetics (such as progabide), alkaloids (such as co-dergocrine, dihydroergocristine, and vincamine); cholinergics (such as citicoline and physosigmine); vasodilators (such as pentoxifyline); and cerebro active agents (such as pyritinol and meclofenoxate); as well as mixtures of several such agents.

Of particular interest are sedative-hypnotics such as the benzodiazepines, psycho-pharmacological agents such as the phenothiazines, thioxanthenes, butyrophenones, and dibenzoxazepines, and central nervous system stimulants. Since, the brain treatment embodiment of the invention is directed to compositions that improve the activity of biological agents, this embodiment of the invention can be applied to a wide variety of central nervous system agents by applying the principles and procedures described herein.

Naturally, a biological agent administered to a subject pursuant to the present invention can also comprise a variety of polypeptides such as antibodies, toxins such as diphtheria toxin, peptide hormones, such as colony stimulating factor, and tumor necrosis factors, neuropeptides, growth hormone, erythropoietin, and thyroid hormone, lipoproteins such as α-lipoprotein, proteoglycans such as hyaluronic acid, glycoproteins such as gonado-tropin hormone, immunomodulators or cytokines such as the interferons or interleukins, hormone receptors such as the estrogen receptor. In a particular embodiment, such polypeptides are those with molecular weight of at least about 500, more preferably at least about 5,000, most preferably at least about 10,000.

Biological agents having applications herein can also comprise enzyme inhibiting agents such as reverse transcriptase inhibitors, protease inhibitors, angiotensin converting enzymes, 5α-reductase, and the like. Typical of these agents are peptide and nonpeptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 39 (17): 3278–90 1966), and didanosine. Such agents can be administered alone or in combination therapy; e.g., a combination therapy utilizing saquinavir, zalcitabine, and didanosine or saquinavir, zalcitabine, and zidovudine. See, for example, Collier et al., *Antiviral Res.*, 1996 Jan. 29 (1):99.

Likewise, a variety of human and animal cytokines are suitable for use as biological agents in the present compositions. These include interferons, interleukins, tumor necrosis factors (TNFs) such as TNFα, and a number of other protein and peptide factors controlling functions of the immune system. It will be appreciated that this extends to mixtures of several such agents, and the invention is not directed to the underlying specific activity of the cytokines themselves, but rather to the compositions themselves.

VII. Carriers

A variety of carriers can be associated with a Ligand of the present invention, including, but not limiting by synthetic, semi-synthetic and natural compounds such as polypeptides, lipids, carbohydrates, polyamines, synthetic polymers, that form solutions (unimolecular systems), dispersions (supramolecular systems), or any particular systems such as nanoparticles, microspheres, matrixes, gels and other.

The following classes of carriers are given as examples. It is understood, however, that a variety of other carriers can be used in the present invention.

The polymeric carriers can be nonionic water-soluble, nonionic hydrophobic or poorly water soluble, cationic, anionic or polyampholite, such as a polypeptides. It is preferred that the degrees of polymerization of these polymer carriers were from about 3 to about 500,000 more preferably from about 5 to about 5000, still more preferably from about 20 to about 500.

A preferred hydrophilic carrier is a nontoxic and non-immunogenic polymer that is soluble in water. Such segments include, but certainly not are limited to polyethers (e.g., polyethylene oxide), polysaccharides (e.g., dextran), polyglycerol, homopolymers and copolymers of vinyl monomers (e.g., polyacrylamide), polyacrylic esters (e.g., polyacryloyl morpholine), polymethacrylamide, poly(N-(2-hydroxypropyl)methacrylamide, polyvinyl alcohol, polyvinyl pyrrolidone, polyvinyltriazole, N-oxide of polyvinylpyridine, copolymer of vinylpyridine and vinylpyridine N-oxide) polyortho esters, polyaminoacids, polyglycerols (e.g., poly-2-methyl-2-oxazoline, poly-2-ethyl-2-oxazoline) and copolymers and derivatives thereof.

A preferred nonionic hydrophobic and poorly water soluble segments include polypropylene oxide, copolymers of polyethylene oxide and polyethylene oxide, polyalkylene oxide other than polyethylene oxide and polypropylene oxide, homopolymers and copolymers of styrene (e.g., polystyrene), homopolymers and copolymers isoprene (e.g. polyisoprene), homopolymers and copolymers butadiene (ig., polybutadiene), homopolymers and copolymers propylene (e.g., polypropylene), homopolymers and copolymers ethylene (e.g., polyethylene), homopolymers and copolymers of hydrophobic amino acids and derivatives of amino acids (e.g., alanine, valine, isoleucine, leucine, norleucine, phenylalanine, tyrosine, typtophan, threonine, proline, cysteine, methionone, serine, glutamine, aparagine), homopolymers and copolymers of nucleic acid and derivatives thereof.

Preferred polyanionic carriers include those such as polymethacrylic acid and its salts, polyacrylic acid and its salts, copolymers of methacrylic acid and its salts, copolymers of acrylic acid and its salts, heparin, polyphosphate, homopolymers and copolymers of anionic aminoacids (e.g., glutamic acid, aspartic acid), polymalic acid, polylactic acid, polynucleotides, carboxylated dextran, and the like.

Preferred polycationic carriers include polylysine, polyasparagine, homopolymers and copolymers of cationic aminoacids (e.g., lysine, arginine, histidine), alkanolamine esters of polymethacrylic acid (e.g., poly-(dimethylammonioethyl methacrylate), polyamines (e.g., spermine, polyspermine, polyethyleneimine, polypropyleneimine, polybutileneimine, polypentyleneimine, polyhexyleneimine and copolymers thereof), copolymers of tertiary amines and secondary amines, partially or completely quatemized amines, polyvinyl pyridine and the quatemary ammonium salts of the polycation segments. These preferred polycation segments also include aliphatic, heterocyclic or aromatic ionenes (Rembaum et al., Polymer letters, 1968, 6;159; Tsutsui, T., In Development in ionic polymers -2, Wilson A. D. and Prosser, H. J. (eds.) Applied Science Publishers, London, new York, vol. 2, pp. 167–187, 1986).

Additionally, dendrimers, for example, polyamidoamines of various generations (Tomalia et al., Angew. Chem., Int. Ed. Engl. 1990, 29, 138) can be also used.

Particularly preferred are copolymers selected from the following polymer groups:

(a) segmented copolymers having at least one hydrophilic nonionic polymer and at least one hydrophobic nonionic segment ("hydrophilic-hydrophobic copolymers");

(b) segmented copolymers having at least one cationic segment and at least one nonionic segment ("cationic copolymers");

(c) segmented copolymers having at least one anionic segment and at least one nonionic segment ("anionic copolymers");

(d) segmented copolymers having at least one polypeptide segment and at least one non-peptide segment ("polypeptide copolymers");

(e) segmented copolymers having at least one polynucleotide segment and at least one segment which is not a nucleic acid "polypeptide copolymers");

Typical representatives of hydrophilic-hydrophobic copolymers are the block copolymers of ethylene oxide and propylene oxide having the formulas:

A. Conolvmers of Ethylene Oxide and Pronvlene Oxide.

In one preferred embodiment, the segmented copolymers are the block copolymers of ethylene oxide and propylene oxide having the formulas:

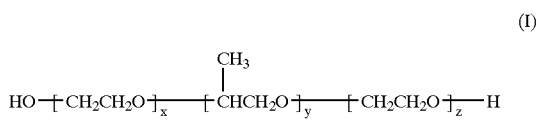

$$HO-(CH_2CH_2O)_x-(CHCH_2O)_y-(CH_2CH_2O)_z-H \quad \text{(I)}$$
$$\phantom{HO-(CH_2CH_2O)_x-(}\overset{|}{CH_3}$$

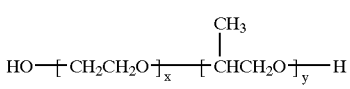

(II)

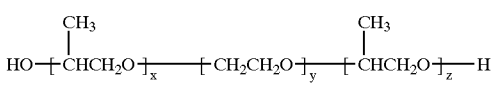

(III)

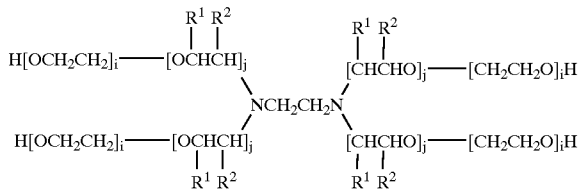

(IV)

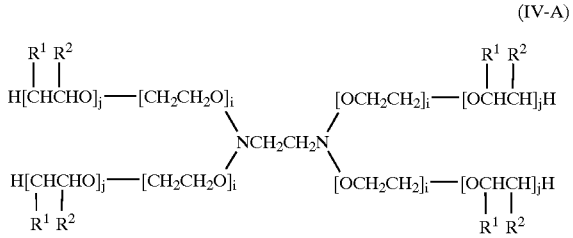

(IV-A)

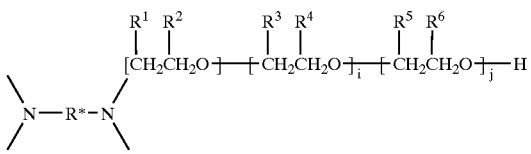

(V)

in which x, y, z, i and j have values from about 2 to about 800, preferably from about 5 to about 200, more preferably from about 5 to about 80, and wherein for each $R^1$, $R^2$ pair, one is hydrogen and the other is a methyl group.

Formulas (I) through (III) are oversimplified in that, in practice, the orientation of the isopropylene radicals within the B block will be random. This random orientation is indicated in formula (IV), which is more complete. Such poly(oxyethylene)-poly(oxypropylene) compounds have been described by Santon, Am. Perfumer Cosmet., 72(4): 54–58 (1958); Schmolka, Loc. cit. 82(7):25 (1967); Schick, Non-ionic Surfactants, pp. 300–371 (Dekker, N.Y., 1967). A number of such compounds are commercially available under such generic trade names as "poloxamers", "pluronics" and "synperonics." Pluronic polymers within the B-A-B formula are often referred to as "reversed" pluronics, "Pluronic-R" or "meroxapol." The "polyoxamine" polymer of formula (XVII) is available from BASF (Wyandotte, Mich.) under the tradename Tetronic™. The order of the polyoxyethylene and polyoxypropylene blocks represented in formula (XVII) can be reversed, creating Tetronic-R™, also available from BASF. See, Schmolka, J. Am. Oil Soc., 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename PluradotTm.

The diamine-linked pluronic of formula (IV) can also be a member of the family of diamine-linked polyoxyethylene-polyoxypropylene polymers of formula:

wherein the dashed lines represent symmetrical copies of the polyether extending off the second nitrogen, $R^*$ is an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

Those of ordinary skill in the art will recognize, in light of the discussion herein, that even when the practice of the invention is confined, for example to poly(oxyethylene)-poly(oxypropylene) compounds, the above exemplary formulas are too confining. Thus, the units making up the first block need not consist solely of ethylene oxide. Similarly, not all of the B-type block need consist solely of propylene oxide units. Instead, the blocks can incorporate monomers other than those defined in formulas (I)–(V), so long as the parameters of the first embodiment are maintained. Thus, in the simplest of examples, at least one of the monomers in block A might be substituted with a side chain group as previously described.

A variety of other examples of hydrophilic-hyrophobic block copolymers have been synthesized that can be used in the present invention. These copolymers have the general formula $A_nB_m$, wherein A is the hydrophilic homopolymer or copolymer segment, and B is a hydrophobic homopolymer or copolymer segment; n is number of units in block A, and m is number of units in block b. Each of the A and B segments can be either straight chain or branched. Examples of block copolymers that are particularly useful in the current invention include, but are not limited to poly (ethylene oxide)-b-poly(isoprene)-b-poly(ethylene oxide) triblock copolymer (Morgan, et al., Biochem. Soc. Trans., 18:1021, 1990), poly(ethylene oxide)-b-poly(styrene) block copolymer (Dunn, et al., Pharm. Res., 11:1016, 1994), poly(ethylene oxide)-b-poly(D,L-lactide) diblock copolymer (Hagan, et al. Langmuir 12:2153, 1996), and poly (ethylene oxide)-b-poly((-benzyl L-aspartate) diblock copolymer (Kwon, et al. Langmuir 12:945, 1993).

The hydrophilic homopolymer or copolymer A segments in hydrophilic-hyrophobic block copolymers that can be used in the present invention will contain at least three monomeric units, each of which unit will have the same or different pendant group. Each pendant group will contain at least one atom selected from the group consisting of oxygen and nitrogen. Representative hydrophilic homopolymers or copolymers include but are not limited to polyethylene oxides, copolymers of ethylene oxide and propylene oxide, polysaccharides, polyacrylamides, polyglycerols, polyvinylalcohols, polyvinylpyrrolidones, polyvinylpyridine N-oxides, copolymers of vinylpyridine N-oxide and vinylpyridine, polyoxazolines, and polyacroylmorpholines.

Preferably, the hydrophilic A segment is:

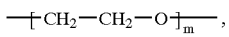

a copolymer of

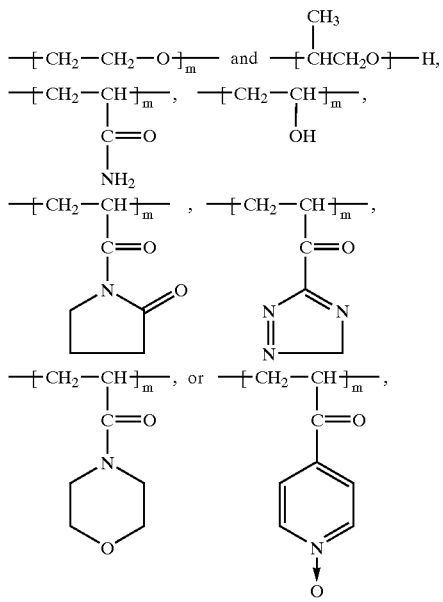

in which each of m and j has a value of from 3 to 5000.

The hydrophobic B segments useful in this invention can also contain fluorocarbon moieties including but not limited to fluoroalkyl segments, and copolymers containing both fluorocarbon and hydrocarbon. One such example is the segmented block copolymers having the formula:

$$R^1-L^1-\{R^2-L^2-A\}w-L^4-R^4-L^3-R^3 \quad (VI)$$

in which:
either, (i) $R^1$ is a monovalent fluorinated hydrocarbon of 2 to 50 carbon atoms and $R^2$ is a divalent hydrocarbon of 2 to 50 carbon atoms or (ii) $R^1$ is a monovalent hydrocarbon of 2 to 50 carbon atoms and $R^2$ is a divalent fluorinated hydrocarbon of 2 to 50 carbon atoms; $R^3$ is (i) hydrogen, (ii) a monovalent fluorinated hydrocarbon of 2 to 50 carbon atoms, or (iii) a monovalent hydrocarbon of 2 to 50 carbon atoms;
$R^4$ is (i) a bond if $R^3$ is hydrogen; (ii) a divalent hydrocarbon of 2 to 50 carbon atoms if $R^3$ is a fluorinated hydrocarbon, or (iii) a divalent fluorinated hydrocarbon of 2 to 50 carbon atoms if $R^3$ is a hydrocarbon; each of $L^1$ and $L^2$, independently of the other, is a linking group; $L^3$ and $L^4$ taken together with $R^4$, is a bond if $R^3$ is hydrogen or if $R^3$ is other than hydrogen each of $L^3$ and $L^4$, taken independently is a linking group;
A is a hydrophilic homopolymer or copolymer comprising at least three monomeric units each having the same or different pendant group containing at least atom selected from the group consisting of oxygen and nitrogen; and w has a value of from 1 to 100.

The hydrophilic homopolymer or copolymer A will contain at least three monomeric units, each of which unit will have the same or different pendant group. Each pendant group will contain at least one atom selected from the group consisting of oxygen and nitrogen. Representative hydrophilic homopolymers or copolymers include polyethylene oxides, copolymers of ethylene oxide and propylene oxide, polysaccharides, polyacrylamides, polyglycerols, polyvinylalcohols, polyvinylpyrrolidones, polyvinylpyridine N-oxides, copolymers of vinylpyridine N-oxide and vinylpyridine, polyoxazolines, and polyacroylmorpholines.

B. Cationic Copolymers

Useful segmented copolymers include a class of copolymers in which at least one segment is a polycation. One example of these structures is a basis of copolymers comprising a plurality of covalently bound polymer segments wherein the segments have (a) at least one polycation segment which segment is a cationic homopolymer, copolymer, or block copolymer comprising at least three aminoalkylene monomers, the monomers being selected from the group consisting of at least one of the following:
(i) at least one tertiary amino monomer of the formula:

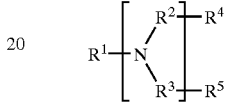

A.

and the quaternary salts of the tertiary amino monomer, or
(ii) at least one secondary amino monomer of the formula:

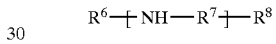

B.

and the acid addition and quaternary salts of the secondary amino monomer, in which:
$R^1$ is hydrogen, alkyl of 2 to 8 carbon atoms, an A monomer, or a B monomer; each of $R^2$ and $R^3$, taken independently of the other, is the same or different straight or branched chain alkanediyl group of the formula:

$$-(C_zH_{2z})-$$

in which z has a value of from 2 to 8; $R^4$ is hydrogen satisfying one bond of the depicted geminally bonded carbon atom; and $R^5$ is hydrogen, alkyl of 2 to 8 carbon atoms, an A monomer, or a B monomer; $R^6$ is hydrogen, alkyl of 2 to 8 carbon atoms, an A monomer, or a B monomer; $R^7$ is a straight or branched chain alkanediyl group of the formula:

$$-(C_zH_{2z})-$$

in which z has a value of from 2 to 8; and $R^8$ is hydrogen, alkyl of 2 to 8 carbon atoms, an A monomer, or a B monomer; and at least one straight or branched nonionic hydrophilic segment A having from about 5 to about 1000 monomeric units which is defined above.

The polycationic segments in the copolymers of the invention can be branched. For example, polyspermine-based copolymers are branched. The cationic segment of these copolymers was synthesized by condensation of 1,4-dibromobutane and N-(3-aminopropyl)-1,3-propanediamine. This reaction yields highly branched polymer products with primary, secondary, and tertiary amines.

An example of branched polycations are products of the condensation reactions between polyamines containing at least 2 nitrogen atoms and alkyl halides containing at least 2 halide atoms (including bromide or chloride). In particular, the branched polycations are produced as a result of polycondensation. An example of this reaction is the reaction between N-(3-aminiopropyl)-1,3-propanediamine and 1,4-dibromobutane, producing polyspermine.

Another example of a branched polycation is polyethyleneimine represented by the formula:

$$(NHCH_2CH_2)_x[N(CH_2CH_2)CH_2CH_2]_y \quad (VI)$$

One example of useful polyamine-based copolymers is the polymer of formula:

$$K^1-L^1-[G-L^2-F-L^3]_l-K^2, \quad (VII)$$

in which:
F is a polyamine segment comprising a plurality of repeating units of formula —NH—$R^0$, wherein $R^0$ is an aliphatic group of 2 to 6 carbon atoms, which may be substituted;

G is polyethylene oxide or copolymer ethylene oxide and propylene oxide a straight or branched nonionic segment defined above;

$K^1$ and $K^2$ independently of the other, is hydrogen, hydroxyl group, amonogroup, G or F polymer segments;

and each of $L^1$, $L^2$ and $L^3$, independently of the other, is a linking group or chemical bond.

The amino groups of polycationic segments can be quaternized to produce ammonium salts. Examples include polyspermine and polyamines that are modified with alkylhalides to produce tertiary and quaternized polyamines. Another useful type of cationic segments of well defmed chemical structure are ionenes that can be aliphatic, heterocyclic or aromatic (Rembaum et al. *Polymer Letters*, 1968, 6:159; Tsutsui, T., Development in ionic polymers-2. Wilson, A. D. and Prosser, H. J. (eds.), Applied Science Publishers, London, New York, vol. 2, pp. 163–187, 1986).

C. Anionic Copolymers

Anionic copolymers contain at least one polyelectrolyte segment that yields a polyanion in an aqueous environment. This includes both strong polyacids having high ionization degrees in a broad range of pH, and weak polyacids characterized by pH-dependent ionization degrees. Anionic segments normally have a plurality of pendant amino groups such as carboxylic groups, sulfate groups, sulfonate groups, phosphate groups, and the like. Examples of anionic copolymers include but are not limited to polyoxyethylene-b-polymethacrylic acid (Wang, et al., *J. Polym. Sci.*, Part A: Polym. Chem., 30:2251 (1992)), polystyrene-b-polyacrylic acid (Zhong, et al. *Macromolecules*, 25:7160, 1992), polyacrylic acid grafted with polyoxyethylene-b-polyoxypropylene-b-polyoxyethylene (Bromberg and Levin, Macromol. Rapid Commun. 17:169 (1996)).

D. Polypeptide Copolymers

Polypeptide copolymers have a plurality of covalently bound polymer segments wherein the segments have at least one polypeptide segment and at least one non-peptide polymer segment. Polypeptide segments have a plurality of amino acid units or derivatives thereof.

Examples of useful segmented copolymers containing polypeptides include the poly(oxyethylene)-poly-L-lysine) diblock copolymer of the following formula:

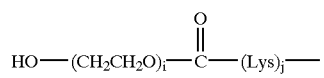

(XVIII)

wherein i is an integer of from about 2 to about 500, andj is an integer from about 4 to about 500. A second example is the poly(oxyethylene)-poly-(L-alanine-L-lysine) diblock copolymer of formula:

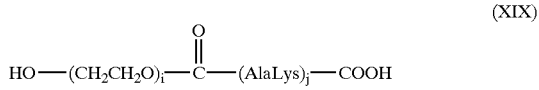

(XIX)

wherein i is an integer of from about 2 to about 500, andj is an integer from about 2 to about 500.

The use of polypeptide copolymers in the invention allows for better control of the polypeptide segment lengths by using solid-phase and solution-phase chemistries. Segmented copolymers based on polypeptides with well defined chemical structures have been described in the literature, such as poly(amino acid)-b-poly(N,N-diethylacrylamide)-b-poly(amino acid) (Bromberg and Levin, *Bioconjugate Chem.* 9:40 (1998)). Further, the unit composition and sequence in polypeptides can be varied including hydrophobic, hydrophilic, ionizable, hydrogen and chemical bond forming amino acids and derivatives thereof to produce broader variability in the basis of the segmented copolymers.

E. Polvnucleotide Copolymers

Polynucleotide copolymers have a plurality of covalently bound polymer segments wherein the segments have at least one segment containing at least three nucleic acid units or the derivatives thereof. Similar to polypeptide copolymers, the polynucleotide copolymers provide for better control over segment length and sequence by using solid-phase and solution-phase chemistries. Segmented copolymers based on polynucleotides with well-defined chemical structure have been described including, polyoxyethylene-b-polynucleotide copolymer and polycation-b-polynucleotide copolymer (Vinogradov et al., *Bioconiugate Chemistry*, 7:3 (1996); U.S. Pat. No. 5,656,611). As with polypeptide copolymers, polynucleotide copolymers permit variation of the unit composition and sequence in polynucleotide segments that is particularly useful in selecting proper biological agent compositions pursuant to this invention.

VIII. Associating Biological Agents and/or Carriers with a Ligand

A. Conjugation of the Ligand

In another embodiment, the present invention provides a Ligand of the present invention conjugated to a biological agent. Particular biological agents having applications herein are described above.

In yet another embodiment, the present invention provides a Ligand conjugated to a drug carrier system, such a carrier system being a polymer molecule, a block copolymer molecule, or a derivative of said polymer. The carrier system may also comprise a protein molecule. Particular carrier systems are described above.

B. Methods of Chemical Conjugation.

The preparation of the conjugates of a Ligand of the present invention to the biological agent, or to the carrier is effected by means of one of the known organic chemical methods for chemical ligation. The structural link between the Ligand and the macromolecule, as well as the chemical method by which they are joined, should be chosen so that the binding ability of the Ligand and the biological activity of the Ligand, when joined in the conjugate, are minimally compromised. As will be appreciated by those skilled in the art, there are a number of suitable chemical conjugation methods. The selection of the appropriate conjugation method can be rationalized by the inspection of the chemical groups present in the conjugated molecules, as well as evaluation of possible modification of these molecules to introduce some new chemical groups into them. Numerous chemical groups can subject conjugation reactions. The following groups are mentioned here as examples: hydroxyl group (—OH), primary and secondary amino group (—NH$_2$ and —NH—), carboxylic group (—COOH), sulfhydryl group (—SH), aromatic rings, sugar residues, aldehydes (—CHO), aliphatic and aromatic halides, and others. Reactivity of these groups is well known in the art (Morrison and Boyd, Organic Chemistry, 6$^{th}$ Ed. (Prentice Hall, 1992), Jerry March, Advanced Organic Chemistry, 4$^{th}$ Ed. (Wiley 1992), which are herein incorporated by reference). A more extensive description of conjugation methods and techniques can be found in: G. T. Harmanson, Bioconjugate Techniques, Academic Press, Inc.1995, and in: S. S. Wong, Chemistry of Protein Conjugation and Cross-Linking, CRC Press, Inc. 1991, which are herein incorporated by reference.

C. Conjugation with Hydroxyl Group

A hydroxyl group (—OH) is present in peptides and proteins in side chains of serine, threonine, and tyrosine residues, and in sugar residues in saccharides and glycoproteins. A hydroxyl group is also present in many chemical compounds, including biological agents such as paclitaxel, and in polymeric compounds, such as polysaccharides and poloxamers. Hydroxyl groups exhibit nucleophilic properties and are subject substitution reactions such as, for example alkylation (etherification), and acylation (esterification). The following reactive chemicals are preferred to conjugate with hydroxyls: alkyl halides (R—Cl, R—Br), cyanogen bromide (CNBr), acyl anhydrides, acyl halides, aldehydes (—CHO), hydrazides (R—CO—NH—NH$_2$), and others. Particularly preferred are: acyl anhydrides ((R—CO)$_2$O), and 1,1'-Carbonyldiimidazole (see, Anderson, G. W. and Paul, R., (1958) *J. Am. Chem. Soc.*, 80, 4423, which is herein incorporated by reference).

D. Conjuation with Amino Group

An amino group (—NH$_2$) is present in peptides and proteins at their N-terminus, if these are not acylated, and in side chains of lysine residues. Amino group is also present in many chemical compounds, including therapeutic agents such as doxorubicin. Chemical and genetic methods allow for introduction of amino group into numerous other molecules, including peptides, proteins, small organic molecules and polymeric molecules. An amino group reveals nucleophile properties, and is subject to a substitution reaction such as, for example alkylation, acylation, and condensation with aldehydes. The following reactive chemicals are preferred to conjugate with amines: alkyl halides (R—Cl, R—Br, R—I), aryl azides, acyl anhydrides, acyl halides, acyl esters, carboxylates activated with carbodiimides, aldehydes (—CHO), and others. Particularly preferred are: acyl anhydrides ((R—CO)$_2$O), acyl chlorides (R—CO—Cl), p-nitrophenyl esters (R—CO—O—C$_6$H$_4$—NO$_2$), N-hydroxysuccinimidyl esters (NHS esters, R—CO—O—N(CO—CH$_2$)$_2$), imidoesters (R—C(=NH)—O—CH$_3$), and carboxylic acids activated with carbodiimides (R—CO—OH+R'—N=C=N—R").

E. Conjugation with Sulfhydryl Group

A sulfhydryl group (—SH) is present in peptides and proteins comprising cysteine residues. A sulfhydryl group is also present in many chemical compounds, and can be introduced into other compounds (see for example Carlsson, J., Drevin, H. and Axen, R. (1978) *Biochem. J.* 173, 723). A sulfhydryl group is subject to electrophonic substitution reactions, for example alkylation, and oxidation reaction. Preferred are the following reactive chemicals, useful to conjugate with -SH group: alkyl iodides, α-unsaturated acyls, and oxidizing agents. Particularly preferred are the following derivatives: iodoacetamides R—CO—CH$_2$—I, maleimides (R—N(CO—CH)$_2$), vinylsulfones (R—SO$_2$—CH=CH$_2$), Masri M. S. (1988). *J. Protein Chein.* 7:49–54, which is herein incorporated by reference), dithiopyridyls (R—S—S-2-pyridyl).

F. Conjugation with Carboxyl Group

Carboxyl group (—COOH) is present in peptides and proteins at their C-terminus (if not amidated), and in side chains of aspartic acid and glutamic acid residues. Carboxyl group is also present in many chemical compounds, including therapeutic agents such as methotrexate. Chemical and genetic methods allow for introduction of a carboxyl group into numerous other molecules, including peptides, proteins, small organic molecules and polymeric molecules. Carboxyl group is able to acylate nucleophilic groups, such as amines and hydroxyls. Carboxyl group requires activation prior to conjugation. The preferred methods of activation are: reaction with organic or inorganic acid halides (for example pivaloyl chloride, ethyl chloroformate, thionyl chloride, PCl$_5$), reaction with carbodiimides (R—CO—OH+R'—N=C=N—R", for example EDC, DCC), reaction with benzotriazolyl uronium or phosphonium salts (TBTU, BOP, PyBOP).

G. Conjugation with Cross-linking Reagents

In preferred embodiment the conjugation of the Ligand receptor to other molecules, either a therapeutic agent or a drug carrier molecule, is achieved with the support of cross-linking reagent. Particularly preferred are heterobifunctional cross-linking reagents. Variety of cross-linking regents is known to those skilled in the art (see, for example, S. S. Wong, Chemistry of Protein Conjugation and Cross-Linking, CRC Press, Inc. 1991, which are herein incorporated by reference).

Heterobiftinctional reagents are particularly useful for linking two molecule, one of them having amino group, and the other having sulfhydryl group. In a preferred embodiment the Ligand has a sulfhydryl group, and therefore is available for conjugation with variety of compounds bearing amino group. The following heterobifunctonal cross-linking reagents, for example, conjugate amino to sulfhydryl compounds: GMBS (N-[γ-Maleimidobutyryloxy]succinimide ester, Fujiwara, K., et al. (1988). *J. Immunol. Meth.* 112, 77–83)), SPDP (N-Succinimidyl 3-[2-pyridyldithio] propionate, Carlsson, J., et al. (1978). *Biochem. J.* 173, 723–737), SIA (N-Succinimidyl iodoacetate, Thorpe, P. E., et al. (1984). *Eur. J. Biochem* 140, 63–71.), SVSB (N-Succinimidyl-[4-vinylsulfonyl]benzoate).

Particularly preferred heterobifunctional linkers have polyoxyethylene chain between the two reactive groups. Conjugation with such linkers yields products having hydrophilic junction between the two conjugated molecules, therefore it increases the solubility of the product in aqueous media. The following linkers with polyoxyethylene are mentioned here as examples: N-Maleimido-polyoxyethylene-succinimide ester (Sharewater Polymers, Cat. No. 2D2Z0F02), vinylsulfone-polyoxyethylene-succinimide ester (Sharewater Polymers, Inc. Al, Cat. No. 2Z5B0F02).

The said biological agents may be used in the invention as biologically active substances. They may as well be used as inactivated chemical derivatives of biological agents, i.e. prodrugs that are being converted to the active substances in certain physiological conditions by means of chemical or enzymatic modification of their structure. For example paclitaxel derivatives in which the 2' or 7-hydroxyl group is converted into an ester of a carboxylic acid form a prodrug (Deutsch et al., "Synthesis of congeners and prodrugs. 3. Water-soluble prodrugs of taxol with potent antitumor activity," *J. Med. Chem.*, 32:788–792, 1989.). For example doxorubicin derivative in which its amino group is acylated with a carboxylic group of amino acid derivative forms a prodrug (Breistol K, et al. "Superior therapeutic efficacy of N-L-leucyl-doxorubicin versus doxorubicin in human melanoma xenografts correlates with higher tumour concentrations of free drug." *Eur J. Cancer*. 1999 July;35(7):1143–9.; DeFeo-Jones D, et al. "A peptide-doxorubicin 'prodrug' activated by prostate-specific antigen selectively kills prostate tumor cells positive for prostate-specific antigen in vivo." *Nat Med* 2000 November; 6(11):1248–52).

H. Genetical Fusion of Ligand with Therapeutic Polypeptides

In another embodiment of the invention, natural, modified, or recombinant nucleic acid sequences encoding the Ligand may be ligated to a biological active polypeptide sequence to encode a fusion protein. The general methods suitable for the construction and expression of Ligand fusions with therapeutic proteins are the same as those described herein above for recombinant production of Ligand. Chimeric Ligand-polypeptides may be most conveniently constructed by fusing in-frame the DNA sequence encoding the Ligand of present invention to a cDNA sequence encoding the polypeptide of interest. However, fusion to genomic fragments of therapeutic polypeptides can also be used. Alternatively, PCR techniques can be used to join the two parts of the molecule in-frame with an appropriate vector. Spacer of various length and structure can be inserted between the Ligand sequence and therapeutic protein in order to provide the fusion protein with additional flexibility and preserve the protein folding. The fusions of Ligand of the present invention can be purified by various well-known methods including affinity chromatography and immobilized metal chelate chromatography (Al-Mashikhi et al., *J. Dairy Sci.* 71:1756–1763 (1988)). Suitable fusion partners are as discussed in Section "Biological agents".

I. Introduction of Ligand in Virus Proteins

The Ligand of present invention can be introduced into viral particles in order to change a tropism of virus. Different viruses are capable of being used as vectors for the in vivo transfer and expression of genes. By way of example, retroviruses (RSV, HMS, MMS, and the like), HSV virus, adeno-associated viruses, adenoviruses, vaccinia virus, and the like, may be mentioned.

For example, the targeting of adenoviruses can be provided by construction of chimeric adenovirus fiber protein, which differs from the wild-type coat protein by the introduction of the Ligand amino acid sequence in a conformationally-restrained manner. Such a chimeric adenovirus fiber protein will be able to direct entry into cells of a vector comprising the chimeric fiber protein that is more efficient than entry into cells of a vector that is identical except for comprising a wild-type adenovirus fiber protein rather than the chimeric adenovirus fiber protein.

Desirably, the Ligand encoding sequence is introduced into the fiber protein at the level of gene expression. Such the Ligand amino acid sequence either is introduced in place of adenoviral sequences, or in addition to adenoviral sequences. Regardless of the nature of the introduction, its integration into an adenoviral fiber protein at the level of either DNA or protein, results in the generation of a SEQ. ID. NO.: 6 peptide motif in the chimeric fiber protein.

Redirecting viral vectors to CNS and enhancing of transport through biological barriers can be achieved by using bispesific conjugates produced by chemical linkage of anti-virus antibody to the Ligand of present invention, as described, for example for anti-adenovirus antibody (Haisma HJ., et al., *Cancer Gene Ther*., 2000, Alvarez R D., et al., *Clin. Cancer Res*., 2000). To avoid the limitation of chemical conjugations, genetically fused proteins comprising of anti-fiber knob AB (or cellular adenovirus receptor, CAR) and the Ligand can be produced (Dmitriev I et al., *J. Virol*., 2000).

The following examples are intended merely to illustrate the best mode now known for practicing the invention but the invention is not to be considered as limited to the details of such examples.

IX. Application and Therapeutic Use

A composition comprising a Ligand of the present invention, a biological agent, and/or a carrier can be administered orally, topically, rectally, vaginally, by pulmonary route by use of an aerosol, or parenterally, i.e. intramuscularly, subcutaneously, intraperitoneallly or intravenously. The ligand composition can be administered alone, or it can be combined with a pharmaceutically acceptable carrier or excipient according to standard pharmaceutical practice. For the oral mode of administration, the ligand compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eyedroppers. Such compositions can include mucomimetics such as hyaluronic acid, chondroitin sulfate, hydroxypropyl methylcellulose or poly (vinyl alcohol), preservatives such as sorbic acid, EDTA or benzylchromium chloride, and the usual quantities of diluents and/or carriers. For pulmonary administration, diluents and/or carriers will be selected to be appropriate to allow the formation of an aerosol.

X. Dosage

The dosage for a biological agent in a composition comprising inter alia, a Ligand of the present invention, will be set by the prescribing medical professional considering many factors including the age, weight and condition of the patient and the pharmacokinetics of the agent. Often the amount of the composition of the invention of an agent required for effective treatment may be less than the amount required using the free biological agent.

Generally, the biological agents used in the invention are administered to an animal in an effective amount. The effect of the ligand used in the composition on effectiveness must be considered in determining effective amount. Generally, an effective amount is an amount effective to either (1) reduce the symptoms of the disease sought to be treated or (2) induce a pharmacological change relevant to treating the disease sought to be treated. For cancer, an effective amount includes an amount effective to: reduce the size of a tumor; slow the growth of a tumor; prevent or inhibit metastases; or increase the life expectancy of the affected animal.

In many cases, the metabolites of various biological agents create or enhance the unwanted effects resulting from administering the agent. For example, this is certainly the case for anthracycline-based drugs, where metabolites are believed to lead to cardiotoxicity. See, Mushlin et al., Br. *J. Pharmacol.* 110: 975–982 (1993). The ligand compositions of the invention can reduce the rate of metabolism for biological agents, thereby reducing the potential for harmful side effects.

Penetration of the small intestine or blood brain barrier by a biological agent can be measured by a number of techniques, as will be recognized by those of ordinary skill in the art. Such methods include isotope labeling, assessing animal behavior for the effects of a biological agent, and measuring lethal dosages for drugs with toxic effects that occur at the brain. Such methods further include measuring decreases in the dosage required to elicit the appropriate biological response.

Various antifungal agents successfully treat human fungal infections. However, the therapeutic dose is often a compromise between achieving effective drug levels and avoiding toxic side effects. In recent years, the emergence of drug resistance among intrinsically sensitive species such as *Candida albicans* and the increasing incidence of intrinsically drug resistant species such as *Candida kruset* has prompted a search for newer antifungal agents.

Although fluconazole has a low incidence of side effects, the incidence of resistance is an increasing problem. Delivery vehicles that are effective in enhancing chemotherapeutic activity and reversing resistance to such agents is therefore desirable for this agent, as well as for other antimicrobial agents.

The present invention may be better understood by reference to the following non-limiting Examples, which is provided as exemplary of the invention. The following Examples are presented in order to more fully illustrate the preferred embodiments of the invention. They should in no way be construed, however, as limiting the broad scope of the invention.

EXAMPLES

Example 1

Solid Phase Peptide Synthesis of the Peptides: Ac-Cys-Arg-Val-Leu-Asp-Gly-Asp-Arg-Thr-Arg-Trp-Gly-NH$_2$ (SEQ. ID. NO.: 1), Tamra-Ala-Ser-Ala-Arg-Val-Leu-Asp-Gly-Asp-Arg-Thr-Arg-Trp-Gly-NH$_2$ (SEQ. ID. NO.: 2). Tamra-D-Ala-D-Ser-D-Ala-D-Arg-D-Val-D-Leu-D-Asp-D-Gly-D-Asp-D-Arg-D-Thr-D-Arg-D-Trp-D-Gly-NH$_2$ (SEQ. ID. NO. 3.

The starting material for the synthesis was 0.6 g (0.4 mmol) of Rink Amide resin (4-(2',4'-Dimethoxyphenyl-Fmoc-aminomethyl)-phenoxy resin) substituted at a level of 0.66 mEq per gram of resin (Nova Biochem, CA). Each of the amino acids, starting with C-terminal glycine, was added in sequence in a synthesis cycle comprising the steps of: piperidine deprotection (step 1), coupling (step 2) and ninhydrin test (step 3). If the test showed incomplete coupling, the coupling step was repeated. The synthesis of peptide comprising an amino acid sequence of SEQ. ID. NO.:1 was completed with additional Fmoc-deprotection (step 1), and acetylation (step 4), followed by trifluoroacetic acid cleavage (step 5) and purification (step 6). All the operations were performed in a glass reactor with a glass frit for draining the solvent. The resin was agitated with the solvents and the respective solutions using a shaker rotating the reactor for 180 degree.

1. Fmoc- Deprotection

The Fmoc- protecting group was removed from the starting resin, or from the α-amino nitrogen of the amino acid previously attached to the resin, by treating the resin twice with 20% piperidine in dimethylformamide (DMF) (20 mL) for 3 min, and for 17 min. The resin was then washed six times with 10 mL of DMF, each wash taking one minute.

2. Coupling

The appropriate Fmoc-protected amino acid (2.4 mmol dissolved in 7 mL DMF), benzotriazole-1-yl-oxy-tris-pyrrolidino-phosphonium hexafluorophosphate (PyBOP) (1.25 g dissolved in 3 mL DMF), and diisopropylethylamine (0.84 mL) was added to the resin, and the mixture was agitated for 90 minutes. The resin was washed four times with 10 mL DMF. The amino acid derivatives used are represented in Table 1.

TABLE 1

| Amino acid | Derivative |
| --- | --- |
| Gly | Fmoc-Gly-OH |
| Trp | Fmoc-Trp(Boc)-OH |
| Arg | Fmoc-Arg(Pbf)-OH |
| Thr | Fmoc-Thr(tBu)-OH |
| Asp | Fmoc-Asp(OtBu)-OH |
| Leu | Fmoc-Leu-OH |
| Val | Fmoc-Val-OH |
| Cys | Fmoc-Cys(Trt)-OH |
| Ala | Fmoc-Ala-OH |
| Ser | Fmoc-Ser(tBu)-OH |

3. Ninhydrin Test

A small sample of resin (approximately 30 beads) was transferred to a test tube. One drop of 1% ninhydrin solution in ethanol, one drop of 80% aqueous phenol, and one drop of 0,001% KCN in pyridine were added to the sample of resin, and the mixture was heated to 120° C. for 5 min. Blue color of beads showed incomplete coupling. In this case the coupling step 2 was repeated. If complete, the synthesis proceeded to the next cycle.

4. Acetylation of Peptide SEQ. ID. NO.:1

After completion of the last cycle with Cys, and Fmoc-deprotection, the resin was agitated with acetic anhydride (0.22 mL) and diisopropylethylamine (0.84 mL) in 5 mL DMF for 90 minutes at room temperature.

5. Labeling of the Peptide SEQ. ID. NO.:2, and SEQ. ID. NO.:3 with Tetramethylrhodamine After completion of the last cycle of peptide chain synthesis, and Fmoc-deprotection, the resin was agitated with 5(and 6-)-tetramethylrhodamine (0.9 g dissolved in 5 mL DMF), PyBOP (1.25 g dissolved in 3 mL DMF), and diisopropylethylamine (0.84 mL) for 120 min.

6. Cleavage with Trifluoroacetic Acid

The resin was washed 6 times with DMF, twice with DMF/methanol (1:1 v/v), and three times with methanol, and dried in vacuum for 1 hour. A mixture of trifluoroacetic acid (TFA, 8.5 mL), water (0.5 mL), phenol (0.5 mL) and thioanisol (0.5 mL) was added to the dry resin, and was agitated for 5 hours. The liquid was drained, and the resin was washed with 2 mL TFA. Combined liquids were evaporated in a stream of dry nitrogen. The residue was washed twice with 20 mL of anhydrous ether, and the product was dissolved in water (20 mL), and freeze dried.

7. Purification

The lyophilized powder was dissolved in water (10 mg of crude peptide in 2 mL) and loaded onto a Vydac C18 preparative column (25×2.25 cm). The column was eluted with a two-component eluent gradient 0.5% per minute, starting from 10% of solution B in solution A, at flow rate 5 mL/min. Solution A was 0.1% TFA in H20, and solution B was 0.1% TFA in CH$_3$CN. Fractions 60–80 mL after the void volume were pooled together and freeze-dried. The product was then dissolved in CH$_3$COOH:H$_2$O (1:9, v/v, 1 mL per 1 mg of product), and freeze-dried.

TABLE 2

| SEQ. ID. NO.: | Yield [mg] | m/e (double charge) | (triple charge) |
|---|---|---|---|
| 1 | 6 | 739.4 | 492.2 |
| 2 | 5 | 988.1 | 659.9 |
| 3 | 5 | 988.3 | 660.2 |

Example 2

The Transport of the Peptides SEQ. ID. NO.:2, and SEQ. ID. NO.:3 Across Caco-Monolayers Caco-2 cells were cultured in Dulbecco's Modified Eagle Medium (D-MEM) (Life Technologies), supplemented with 10% fetal bovine serum at 37° C. in humidified atmosphere with 5% CO$_2$. The desired numbers of Transwell (6.5 mm diameter, 0.4 μm pore size) were placed in the wells of the tissue culture plates. The filters were wetted with medium (0.1 ml to the apical and 0.6 ml to the basolateral sides of Transwell) for 30 min in the CO$_2$ incubator before the harvest of the cells from the flasks. The cells were re-suspended in the medium 5×10$^5$ cells/ml and 0.2 ml of cell suspension medium was added to the apical side of the Transwell and cultured in the CO$_2$ incubator. The medium was changed every second day for 8–12 days to obtain well-differentiated monolayers suitable for transport experiences.

The cell monolayers on the insert filter apically and basolaterally were rinsed twice on each side with PBS and pre-incubated with pre-warned D-MEM for 30 min. The medium in apical chamber was gently removed. The fresh pre-warmed D-MEM (1.2 ml) was placed to new basolateral chamber ("FALCON" 3504 Tissue Culture Plate). The inserts were transferred to the new chamber. Fluoresceine-labelled dextrane (MW 3000 from Molecular Probes) at concentration 50 micromol/L was used as a probe to monitor Caco-2 monolayer leakiness. Peptide SEQ. ID. NO.: 2, or SEQ. ID. NO.: 3 was added to the apical sides to give the concentration 50 micromol/L. After 0.5, 1, 1.5 and 2 hours incubation, the media from apical and basolateral sides of the chamber was collected and used to determine the peptide and dextrane transport across Caco-2 monolayers. The relative transport of compounds in % through Caco-2 was calculated as:

$$P = Cb/(Ca+Cb) * Vb/Va$$

where Cb is a concentration of compound in basolateral chamber, Ca is a concentration of compound in the apical chamber, Vb is a volume of media in basolateral chamber and Va is a volume of media in the apical chamber. The concentration of peptide in sample was determined by the fluorescence of the sample using excitation 530 nm, emission 590 nm. The concentration of dextran in samples was determined by the fluorescence of the sample using excitation 480 nm, emission 530 nm.

TABLE 3

| Peptide | Transport [%] | | | |
|---|---|---|---|---|
| SEQ. ID. NO.: | 0.5 h | 1.0 h | 1.5 h | 2.0 h |
| 2 | 0.22 | 0.16 | 0.71 | 1.23 |
| 3 | 0.06 | 0.43 | 0.30 | 1.03 |
| dextran | 0.05 | 0.16 | 0.38 | 0.63 |

Digestion of peptide SEQ. ID. NO.:2 in apical chamber was determined using HPLC. The samples were diluted 100 times with the media, and 0.200 mL of each was injected on a column RP-HPLC column Vydac 218TP54, pre equilibrated 15 minutes with 5 acetonitroile/water (10 mM phosphoric acid) at flow rate 1 mL per minute. Sample was eluted with two component gradient 1% per minute of acetonitrole (10 mM phosphoric acid)/water (10 mM phosphoric acid) at flow rate 1 mL per minute. Fluorescent detection was used with excitation wavelength 555 nm and emission wavelength 580 nm. The peptide SEQ. ID. NO.: 2 was eluted as sharp peak at 22.3 min. The percentage of remaining peptide was calculated as:

$$T = A/\text{SUM}(Ai)$$

where A—area under the peak at 22.3 min, SUM(Ai)—the sum of area of all peaks eluted between 13 and 26 minutes.

TABLE 4

| Percentage of remaining peptide SEQ. ID. NO.: 2 after incubation with [%] CACO 2 cells | | | | |
|---|---|---|---|---|
| Time of incubation | 0.5 h | 1 h | 1.5 h | 2 h |
| Remaining peptide [%] | 86 | 84 | 78 | 63 |

Example 3

Construction of the Phage that Expresses a Peptide Comprising an Amino Acid Sequence of SEQ. ID. NO.:4

A peptide comprising an amino acid sequence of SEQ. ID. NO.:4 was expressed as a fuision protein with minor coat protein III of E.coli bacteriophage M13. 100 μg of the phage vector fUSE5, containing Sfi I restriction sites in N-end of pIII, was digested with Sfi I restrictase (Boehringer Mannheim Biochemica) at supplier recommended conditions, purified by phenol:chloroform extraction and isolated from 14-bp stuffer fragment by precipitation with isopropanol for 20 min on ice. The linearized vector contained two non-complementary Sfi I ends, cannot be self ligated and allows oriented ligation of oligonucleotides with the appropriate cohesive ends. The oligonucleotide inserts coding a peptide comprising an amino acid sequence of SEQ. ID. NO.:4 were synthesized by automatic solid phase oligonucleotide synthesis and purified by reverse phase chromatography. The sequence of the oligonucleotide, OLIGO ID. NO.:1, encoding a peptide comprising an amino acid sequence of SEQ. ID. NO.:4 is the following:

GGGCCGGTAGGGTGCTGGACGGTGACCG-GACGCGTTGGGGTGGTGGCGCTTCTG.

The 5'- and 3'- ends of the oligonucleotide comprising a DNA sequence of OLIGO ID. NO.:1was annealed to two "half-site" fragments, OLIGO ID NO 2 and OLIGO ID.

NO.: 3 to form cohesive termini complementary to Sfi I sites 1 and 2 in the vector. Oligonucleotides were phosphorylated with T4 kinase, and annealed in 20 mM Tris-HCl, pH 7.5, 2 mM $MgCl_2$, 50 mM NaCl, by mixing 1.5 µg OLIGO ID NO 2, 1.2 µg OLIGO ID. NO.: 3, and 0.5 µg OLIGO ID. NO.: 1, heating to 65° C. for 5 minutes and allowing the mixture to cool slowly to room temperature. This mixture represented an approximate molar ratio of 5:100:100 (OLIGO ID. NO.:1: OLIGO ID NO.: 2: OLIGO ID. NO.: 3). The annealed oligonucleotide insert (200 ng) was then ligated to 20 µg of Sfi-I-cut fuSE5 RF DNA (molar ratio 1:5) to produce a double-stranded circular molecule with a small, single stranded gap. The annealed DNA was ligated in 20 mM Tris-HCl, pH 7.5, 5 mM MgCl.sub.2, 2 mM DTT, 1 mM ATP, by the addition of 20 units of T4 DNA ligase and incubated overnight at 15° C. The ligated DNA was ethanol precipitated in the presence of 0.3M sodium acetate, resuspended in water and electro-transformed into competent *E. coli* MC1061 cells using a Gene Pulser electroporation apparatus (Bio Rad) at 1,8 kV/cm, 200 Ω, 25 mF. After electroporation, *E.coli* cells were allowed to reparate at 37° C. for 1 hour in 2 ml of SOC medium (2% Bacto tryptone, 0.5% Bacto yeast extract, 10 mM NaCl, 2.5 mM KCl, 10 mM $MgCl_2$, 10 mM MgSO4, 20 mM glucose, 0.2 mg/ml tetracycline) and plated on Petri dishes with Luria-Bertani (LB) agar, containing 100 mg/ml kanamycine and 40 mg/ml tetracycline. Plates were incubated overnight at 37° C. Phage from single colonies were amplified in LB medium and purified using double precipitation with polyethylene glycol, as described in Phage display of peptides and proteins, Ed. By B. Kay et al., Academic Press. San Diego, 1996. The structure of recombinant phage clones was confirmed by dideoxy DNA sequencing.

---

List of oligonucleotide sequences

OLIGO ID NO 1

LENGTH: 54 nucleotides
TYPE: nucleotide
GGGCCGGTAGGGTGCTGGACGGTGACCGG-
ACGCGTTGGGGTGGTGGCGCTTCTG
(SEQ. ID. NO. 8)

OLIGO ID NO 2

LENGTH: 10 nucleotides
TYPE: nucleotide
AAGCGCCACC
(SEQ. ID. NO. 9)

OLIGO ID NO.: 3

LENGTH: 11 nucleotides
TYPE: nucleotide
ACCGGCCCCGT
(SEQ. ID. NO. 10)

---

Example 4

The Transport of a Phage that Expresses a Peptide ComPrising an Amino Acid Sequence of SEQ. ID. NO.:4 Across Caco-2 Monolavers In vitro rates of drug transport across Caco-2 cell monolayers are frequently used to obtain an initial prediction of oral bioavailability for therapeutic compounds. This cell line was established by Fogh in 1977 (Fogh J., et al, *J.Natl. Acad. Sci.* 59 (1977) 221–226) as immortalized cell line derived from human colon carcinoma. Caco-2 cells can grow as a polarized monolayer on porous support and demonstrate morphological characteristics of intestinal epithelium (well-defined brush border on the apical face expressing typical small intestine hydrolases and markers, and well-formed tight junctions between the cells).

Caco-2 cells were cultured in Dulbecco's Modified Eagle Medium (D-MEM) (Life Technologies), supplemented with 10% fetal bovine serum at 37° C. in humidified atmosphere with 5% $CO_2$. The desired numbers of Transwell (6.5 mm diameter, 0.4 µm pore size) were placed in the wells of the tissue culture plates. The filters were wetted with medium (0.1 ml to the apical and 0.6 ml to the basolateral sides of Transwell) for 30 min in the $CO_2$ incubator before the harvest of the cells from the flasks. The cells were re-suspended in the medium $5 \times 10^5$ cells/ml and 0.2 ml of cell suspension medium was added to the apical side of the Transwell and cultured in the $CO_2$ incubator. The medium was changed every second day for 8–12 days to obtain well-differentiated monolayers suitable for transport experiences.

The cell monolayers on the insert filter apically and basolaterally were rinsed twice on each side with PBS and pre-incubated with pre-wanned D-MEM for 30 min. The medium in apical chamber was gently removed. The fresh pre-warmed DMEM (1.2 ml) was placed to new basolateral chamber ("FALCON" 3504 Tissue Culture Plate). The inserts were transferred to the new chamber. $^3$H-Manitol was used as a probe to monitor Caco-2 monolayer leakiness. The medium containing isotope-labeled compound, a phage that expresses a peptide comprising an amino acid sequence of SEQ. ID. NO.:4 ($5 \times 10^9$ cfu/ml) or wild-type phage (Control phage 1, $5 \times 10^9$ cfu/ml), or random peptide phage display library (Control phage 2, $5 \times 10^9$ cfu/ml) was added to the apical side. After 2 hours incubation, the media from apical and basolateral sides of the chamber was collected and used to determine the phage and $^3$H-manitol transport across Caco-2 monolayers. The relative transport of compounds in % through Caco-2 was calculated as:

$$P = Cb/(Ca+Cb) * Vb/Na$$

where Cb is a concentration of compound in basolateral chamber, Ca is a concentration of compound in the apical chamber, Vb is a volume of media in basolateral chamber and Va is a volume of media in the apical chamber. The phage that expresses a peptide comprising an amino acid sequence of SEQ. ID. NO.:4 demonstrated 10,000-fold higher permeability of Caco-2 monolayer, than both control phage samples (Table #5).

TABLE 5

| Analyzed compound | Ca | Cb | Transport through Caco-2 monolayers, P, % | Transport of 3H-Mannitol, P, % |
|---|---|---|---|---|
| Phage expressing a peptide comprising an amino acid sequence of SEQ. ID. NO.: 4 | $5 \times 10^9$ cfu/ml | $2.55 \times 10^7$ cfu/ml | $2.55 \times 10^{-2}$ | 23 |

TABLE 5-continued

| Analyzed compound | Ca | Cb | Transport through Caco-2 monolayers, P, % | Transport of 3H-Mannitol, P, % |
|---|---|---|---|---|
| Control phage 1 | $4.7 \times 10^9$ cfu/ml | $2 \times 10^3$ cfu/ml | $4.25 \times 10^{-7}$ | 21 |
| Control phage 2 | $4.25 \times 10^9$ cfu/ml | $1 \times 10^3$ cfu/ml | $2.35 \times 10^{-7}$ | 27 |

Example 5

The Permeability of a Phage that Expresses a Peptide Comprising an Amino Acid Sequence of SEQ. ID. NO.:4 Across Human Blood-brain Barrier in Vitro The evaluation of the transport of a phage that expresses a peptide comprising an amino acid sequence of SEQ. ID. NO.:4 across the human blood brain barrier (BBB) in vitro was performed using two-chamber model with human cerebromicrovascular endothelial cell (HCEC) monolayers.

HCEC cultures are derived from small samples of human temporal lobe excised surgically from patients treated for idiopathic epilepsy and are routinely isolated and maintained in culture. HCEC demonstrated a polygonal, 'cobblestone' morphology, immunoreactivity for the endothelial cell markers, factor VIII-related antigen and angiotensin-converting enzyme, and high levels of the BBB-specific markers, enzymes GGTP and alkaline phosphatase (ALP), glucose transporter-1 (GLUT-1), HT7 antigen (26, 27), and express MDR-phenotype (mdr-1), an important feature of the BBB.

A compartmentalized BBB model comprises a monolayer of HCEC grown on semi-permeable membranes positioned between two separated compartments. The bottom chamber of the insert assembly contains growth medium supplemented with the fetal human astrocyte (FHAS)-conditioned medium in a 1:1 (v/v) ratio. The FHAS-conditioned medium is obtained by incubating confluent FHAS in a serum free M199 for 72 hr, and has been shown to induce markers of the BBB phenotype in HCEC. An assessment of the functional performance of the compartmentalized BBB model is routinely performed by measuring changes in the transendothelial electrical resistance (TEER) using a Millicel$^R$ ERS system, and by determining paracellular passage of $^3$H-sucrose and $^{14}$C-inulin across HCEC monolayers. The TEER values (300–350 $\Omega/cm^2$), as well as the permeability coefficients, $P_e$, for $^3$H-sucrose and $^{14}$C-inulin were 0.28× $10^{-3}$ and 0.14×$10^{-3}$ respectively. Two sets of internal controls were performed for each 'test compound'. Firstly, Transport of $^3$H-sucrose (2 $\mu$Ci/ml) and $^{14}$C-inulin (0.5 $\mu$Ci/ml) in the absence of test compound were used to assess paracellular transport, whereas the same two radiolabelled markers were also used in the presence of test compounds to assure that compound itself is inert and does not change monolayer permeability. The phage that expresses a peptide comprising an amino acid sequence of SEQ. ID. NO.:4 and a control phage were added into apical chamber to the concentration 1×$10^{10}$ cfu/ml. After 4 hours incubation, the media from apical and basolateral sides of the chamber was collected and used to determine the phage titer. The relative transport of compounds was calculated as described in Example #3. The phage that expresses a peptide comprising an amino acid sequence of SEQ. ID. NO.:4 was able to cross HCEC monolayers with efficacy 1000 fold higher than control phage.

TABLE 6

| Analyzed compound | Ca | Cb | Transport through Caco-2 monolayers, P, % |
|---|---|---|---|
| Phage that expresses a peptide comprising an amino acid sequence of SEQ. ID. NO.: 4 | $1 \times 10^{10}$ cfu/ml | $1.035 \times 10^7 \pm 1.35 \times 10^6$ cfu/ml | $1.035 \times 10^{-3}$ |
| Control phage 1 | $1.07 \times 10^{10}$ cfu/ml | $4 \times 10^4 \pm 1 \times 10^3$ cfu/ml | $3.74 \times 10^{-6}$ |

Example 6

Conjugation of Peptide Comprising an Amino Acid Sequence of SEO. I.D NO.:1 with a Carrier The compounds of the invention are tested for their ability to transport proteins across intestinal barrier. For that purpose a peptide comprising an amino acid sequence of SEQ. ID. NO.: 1 was chemically conjugated to the carrier protein.

The carrier protein, for example horseradish peroxidase (ICN, 250 u/mg) was dissolved in phosphate buffer (0,1M Na2HPO4, 0,1M NaCl, 1mM EDTA and pH 8,5) at final concentration 3 mg/ml. N-succinimidyl-3-(2-pyridylthio) propionate (SPDP, Sigma Chemical) was dissolved in 133,ul of dimethylformamide (DMFA), in a proportion of 0.234 mg SPDP=39 ul DMFA. The solution of SPDP was added to solution of peroxidase and incubated with stirring at room temperature for 30 minutes. After modification, activated protein was purified by gel filtration. The solution of peroxidase was applied to the Sephadex G-25 column (Fisher, 20 ml) and eluted with 50 ml of phosphate buffer. Detect at 280 nm with a sensitivity of 50 and lamp intensity of 0.005 Au. The fractions (1 ml) were collected using a fraction collector (Pharmacia Biotech). The fractions containing modified Peroxidase were selected and combined (total volume of 5–7 ml). An aliquot of 1 ml was kept for the control. A number of activated groups were evaluated by treatment of the aliquot of activated protein with 1 mg/ml of L-cysteine methyl ester hydrochloride (Aldrich Chemical). The amount of recovered 2-pyridyl disulphide was measured by UV absorbency at 343 nm. The control sample was treated with cysteine for 15 hours at room temperature, purified by gel filtration and used as a reference in receptor binding assays. 1 mg of a peptide comprising an amino acid sequence of SEQ. ID. NO.:2, was dissolved in 200 $\mu$l of phosphate buffer. Activated peroxidase was mixed with the peptide and incubated with stirring for 24 hours, at room temperature. The reaction was controlled by UV detection at 343 nm (detection of 2-pyridyl disulphide). The conjugate was purified by gel filtration using a Sephadex G-25 column. The conjugate fractions were collected and combined, and the protein concentration was determined using a Bradford assay (Coomasie blue, Bio-Rad). Conjugation of the peptide comprising an amino acid sequence of SEQ. ID. NO.:1 was confirmed by SDS/PAGE electrophoresis. Peroxidase activity of the conjugate per mg of protein was determined by incubation of conjugate aliquots with ABTS solution (0.22 mg/ml 2'2'-azino-bis-93'-ethylbenzthiazoline-6-sulphonic acid) diammonium salt, 0.05M citric acid, pH 4.0, 0.05% $H_2O_2$) for 30 min at room temperature and detection the absorbance at 405 nm.

Example 7

Transport of a Conjugate Comprising a Peptide Comprising an Amino Acid Sequence of SEO. ID. NO.:1 Across Caco-2 Monolavers

A two-chamber Caco-2 model was used to evaluate the transport of a conjugate comprising peroxidase and a peptide comprising an amino acid sequence of SEQ. ID. NO.:1 across the intestinal barrier (IB) in vitro. Caco-2 cell monolayers were prepared as described in Example 4 above. The medium containing isotope-labeled compound, the SEQ. ID. NO.:1-Peroxidase conjugate (25 g/ml) or Control Peroxidase conjugate (25 g/ml) was added to the apical side of cultured Caco-2 monolayers. After 2 and 4 hours incubation, the media from apical and basolateral sides of the chamber respectively were collected and used to determine peroxidase activity and $^3H$-manitol transport across Caco-2 monolayers. The relative transport of compounds in % through Caco-2 was calculated as:

$$P = Cb/(Ca+Cb)*Vb/Na$$

Where Cb is a concentration of compound in basolateral chamber, Ca is a concentration of compound in the apical chamber, Vb is a volume of media in basolateral chamber and Va is a volume of media in the apical chamber. The SEQ. ID. NO.:1-Peroxidase conjugate demonstrated 2.5-fold higher permeability of Caco-2 monolayer, than both control Peroxidase samples (Table # 4).

TABLE 7

| Analyzed compound | Transport through Caco-2 monolayers, P, % | | Transport of 3H-Mannitol, P, % | |
|---|---|---|---|---|
| | 2 hours | 4 hours | 2 hours | 4 hours |
| SEQ. ID. NO.: 1-Peroxidase Conjugate | 0.35 ± 0.014 | 0.705 ± 0.09 | 6.6 | 12.4 |
| Control Peroxidase | 0.193 ± 0.006 | 0.268 ± 0.011 | 7.3 | 12.7 |

Example 8

The in Vivo Bioavailability of a Phage that Expresses a Peptide Comprising an Amino Acid Sequence of SEQ. ID. NO.:4 After Intraintestinal Administration

Animals: Female Sprague Dawley rats, weighing 150 to 175 g, were received from Charles River Canada Inc. (St. Constant, Quebec, Canada). The animals were kept 3 per cage with an air filter cover under light (12h light/dark cycle, light on at 06h00) and temperature (22°±1° C.)-controlled environment. All manipulations with the animals were performed under a sterilized laminar hood. The animals had ad libitum access to Purina mouse chow (Pro Lab PMH 4018, Trademark of Agway, Syracuse, N.Y.), and water. The animal studies were conducted according to the "Guidelines for Care and Use of Experimental Animals." The animals were randomly divided into two following groups (control phage and phage that expresses a peptide comprising an amino acid sequence of SEQ. ID. NO.:4) and anesthetized with "KETASET" (Wyeth-Ayerst Canada Inc., Ontario). The small intestine was exposed with surgical instruments and the phage sample solutions ($1 \times 10^{11}$ cfu in 200 ul of PBS, pH 7.5) were gently injected into small intestine. The blood samples were collected at 5; 30; 60 and 120 min after the phage administration inside the small intestine. The plasma were immediately prepared and phage titer (cell transducting units per ml of plasma) was determined using E.coli K91Kan competent cells. Results represented in the Table 5 set forth that the that expresses a peptide comprising an amino acid sequence of SEQ. ID. NO.:1 could reach the bloodstream with 10,000 fold higher efficacy than control phage.

TABLE 8

| Time after intraintestinal administration, Min | Phage titer in the blood | |
|---|---|---|
| | Control phage, Cfu/ml | SEQ. ID. NO.: 4 expressing phage Cfu/ml |
| 5 | $1 \times 10^3 \pm 2.8 \times 10^3$ | $5.3 \times 10^6 \pm 2.8 \times 10^5$ |
| 30 | $3.5 \times 10^3 \pm 7 \times 10^2$ | $1.3 \times 10^7 \pm 1.8 \times 10^7$ |
| 60 | $2.75 \times 10^3 \pm 5 \times 10^2$ | $3.92 \times 10^8 \pm 5 \times 10^7$ |
| 120 | $3.1 \times 10^3 \pm 3 \times 10^2$ | $7.88 \times 10^8 \pm 2.72 \times 10^8$ |

Example 9

Pharmacokinetics in the Blood of rats of a Phaee that Expresses a Peptide Comprising an Amino Acid Sequence of SEO. ID. NO.:4 And Distribution in Organs After I.V. Iniection

Female Sprague Dawley rats, weighing 150 to 175 g Rats (3 per group) were injected I.V. with $10^{12}$ cfu/100 µl of either a phage that expresses a peptide comprising an amino acid sequence of SEQ. ID. NO.:4 or a control phage. Blood samples were collected in 5 min, 30 min, 1 h and 2 hours after injection. Phage titer in the blood samples was detected (Table 5). After 24 h, the animals were sacrificed and the brain, heard, liver, lung and kidney of the animals were harvested. Each of these organs for each animal was homogenized, and the titer of phage in the organs (cell transducting units per gram of tissue) was determined as described in Pasqualini R. et. al., Nature 380:364–366 (1996). The organ biodistribution of phage is presented in the Table 6. A high accumulation of the phage that expresses a peptide comprising an amino acid sequence of SEQ. ID. NO.:4 was detected in the brain, kidney, lung and the heart of analyzed animals. The 80-fold higher accumulation of the phage that expresses a peptide comprising an amino acid sequence of SEQ. ID. NO.:4 was detected in the brain compared levels of control phage detected in the brain. The maximum accumulation of phage in rats injected with the ligand-expressing phage was determined in the brain (ratio brain:liver=18.1). Control phage was more equally distributed in the organs and did not accumulated in the brain (ratio brain:liver=0.31)

TABLE 9

| Time after I.V. injection, Min | Phage titer in the blood | |
|---|---|---|
| | Control phage, Cfu/ml | SEQ. ID. NO.: 4 expressing phage Cfu/ml |
| 5 | $2.12 \times 10^{10} \pm 1.1 \times 10^{10}$ | $2.87 \times 10^{10} \pm 6.93 \times 10^{9}$ |
| 30 | $1.32 \times 10^{10} \pm 4.05 \times 10^{9}$ | $2.38 \times 10^{10} \pm 5.77 \times 10^{9}$ |
| 60 | $3.92 \times 10^{9} \pm 1.05 \times 10^{9}$ | $1.15 \times 10^{10} \pm 7.66 \times 10^{9}$ |
| 120 | $2.57 \times 10^{9} \pm 1.1 \times 10^{9}$ | $4.62 \times 10^{9} \pm 3.12 \times 10^{9}$ |

TABLE 10

| Organ | SEQ. ID. NO.: 4-expressing phage CFU × $10^6$/g of tissue | Control phage CFU × $10^6$/g of tissue |
|---|---|---|
| Liver | 10.6 ± 3.9 | 7.37 ± 3.01 |
| Kidney | 73 ± 40.7 | 4.03 ± 1.88 |
| Brain | 192 ± 69.4 | 2.31 ± 1.27 |
| Lung | 117 ± 76.5 | 7.69 ± 3.06 |
| Heart | 206 ± 16.4 | 16.4 ± 13.5 |
| Spleen | 43.2 ± 27.1 | 11.1 ± 4.79 |

Example 10

The Inhibition of a Transport Across Caco-2 Monolavers of a Phage Expressing a Peptide Seguence SEO. ID. NO.:4 by Using SEQ. ID. NO.:1-Peroxidase Conjugate Caco-2 cells were cultured in Dulbecco's Modified Eagle Medium (D-MEM) (Life Technologies), supplemented with 10% fetal bovine serum at 37° C. in humidified atmosphere with 5% $CO_2$ and grown in Transwell system as described in Example 4.

The cell monolayers on the insert filter apically and basolaterally were rinsed twice on each side with PBS and pre-incubated with pre-warmed D-MEM for 30 min. The medium in apical chamber was gently removed. The fresh pre-warmed D-MEM (1.2 ml) was placed to new basolateral chamber ("FALCON" 3504 Tissue Culture Plate). The inserts were transferred to the new chamber. $^3$H-Manitol was used as a probe to monitor Caco-2 monolayer leakiness. The medium containing isotope-labeled compound, a phage that expresses a peptide comprising an amino acid sequence of SEQ. ID. NO.:4 ($5 \times 10^9$ cfu/ml) or wild-type phage (Control phage $1.5 \times 10^9$ cfu/ml) in the presence and absence of 50 μg/ml of SEQ. ID. NO.:1-Peroxidase conjugate was added to the apical side. After 3 hours incubation, the media from apical and basolateral sides of the chamber was collected and used to determine the phage and $^3$H-manitol transport across Caco-2 monolayers. The relative transport of compounds in % through Caco-2 was calculated as:

$$P = Cb/(Ca+Cb) * Vb/Va$$

where Cb is a concentration of compound in basolateral chamber, Ca is a concentration of compound in the apical chamber, Vb is a volume of media in basolateral chamber and Va is a volume of media in the apical chamber. The transport of phage that expresses a peptide comprising an amino acid sequence of SEQ. ID. NO.:4 was completely inhibited by peptide SEQ. ID. NO.: 1-Peroxidase conjugate, suggesting that the Ligand of present invention transports the phage across Caco-2 monolayers by Ligand-dependent, receptor-mediated mechanism. No effect on paracellular transport of $^3$H-Mannitol in the presence of the phage expressing a peptide comprising an amino acid sequence of SEQ. ID. NO.:4, or peptide SEQ. ID. NO.:1-Peroxidase conjugate was detected.

TABLE 11

| Analyzed compound | Concentration of phage in basolateral chamber, cfu/ml | Transport of 3H-Mannitol, % per h |
|---|---|---|
| Phage expressing a peptide comprising an amino acid sequence of SEQ. ID. NO.: 4 | $3.92 \times 10^7$ | 2.70 |
| Control phage 1 | $1.75 \times 10^4$ | 2.9 |
| Phage expressing a peptide comprising an amino acid sequence of SEQ. ID. NO.: 4 + 50 g/ml peptide SEQ. ID. NO.: 1-Peroxidase conjugate | $5 \times 10^4$ | 2.6 |
| Control phage 1 + 50 μg/ml peptide SEQ. ID. NO.: 1-Peroxidase conjugate | $1.50 \times 10^4$ | 2.73 |
| Media | | 2.75 |

Example 11

Alanine Substitution Mutations

The single point mutations in the phage insert coding amino acid sequence SEQ. ID. NO.:4 were produced as described previously in Hoess, R., et al, *Gene*, 128:43–49 (1993). Briefly, a series of SEQ. ID. NO.:4 coding oligonucleotides in with a particular amino acid coding triplet was changed to GCT (alanine coding triplet) were synthesized. Mutated oligonucleotides were cloned in to fUSE5 phage vector as described in Example 3. All mutant phage clones were purified and verified by DNA sequencing.

The transport of mutated phage clones through Caco-2 cell monolayers was analysed as described in Example 4.

TABLE 12

| Phage Clone | INSERT SEQUENCE | Transport of phage in % |
|---|---|---|
| SEQ. ID. NO: 4 | RVLDGDRTRWG | 3.39E-03 ± 1.3E-03 |
| R1/A (SEQ. ID. NO.: 11) | AVLDGDRTRWG | 1.50E-04 ± 2.19E-05 |
| V2/A (SEQ. ID. NO.: 12) | RALDGDRTRWG | 8.39E-06 ± 0 |
| L3/A (SEQ. ID. NO.: 13) | RVADGDRTRWG | 9.92E-06 ± 0 |
| D4/A (SEQ. ID. NO.: 14) | RVLAGDRTRWG | 1.79E-04 ± 1.63E-05 |
| G5/A (SEQ. ID. NO.: 15) | RVLDADRTRWG | 2.76E-03 ± 2.06E-03 |
| D6/A (SEQ. ID. NO.: 16) | RVLDGARTRWG | 1.15E-04 ± 9.05E-05 |
| R7/A (SEQ. ID. NO.: 17) | RVLDGDATRWG | 8.81E-03 ± 9.05E-05 |
| T8/A (SEQ. ID. NO.: 18) | RVLDGDRARWG | 4.04E-05 ± 1.17E-05 |
| R9/A (SEQ. ID. NO.: 19) | RVLDGDRTAWG | 5.7E-03 ± 1.6E-03 |
| W10/A (SEQ. ID. NO.: 20) | RVLDGDRTRAG | 4.0E-03 ± 2.24E-04 |
| G11/A (SEQ. ID. NO.: 21) | RVLDGDRTRWA | 2.70E-04 ± 8.68E-06 |
| D46/A (SEQ. ID. NO.: 22) | RVLAGARTRWG | 2.70E-04 ± 8.68E-06 |
| R79/A (SEQ. ID. NO.: 23) | RVLDGDATAWG | 2.64E-04 ± 2.54E-4 |
| Control | Library | 7.45E-06 ± 3.71F-06 |

Example 12

Association of SEQ. ID. NO.:4 with Erythropoietin

The murine erythropoietin (mEPO) gene was cloned in pcDNA/Amp1.1 expression vector using RT/PCR. CDNA encoded mEPO was obtained by reverse transcription of mRNA extracted from kidneys of mice treated for 3 days with phenylhydrazine (Shoemaker CB., et al., *Mol.Cel.Biol.* (1986)). Amplification of DNA was performed using the sense 5'-ATAACAAGCTTGGCGCGGAGATGGGGGTG (SEQ.ID.NO.:24) and antisense 5'-ATAACTCTAGAACG GTGGCAGCAGCATGTCAC (SEQ.ID.NO.:25) primers. The amplified mEPO gene was inserted into the XbaI and Hind III sites of pcDNA/Amp1.1, and sequence was confirmed by DNA sequencing. Cos-7 cells were transfected with pCMV/EPO plasmide, and expression of recombinant mEPO was evaluated by Quantikine IVD Erythropoietin ELISA kit. The physiological activity of recombinant mEPO was evaluated in vivo by measured of hematocrit.

Synthetic oligonucleotide encoded peptide SEQ. ID. NO.:4 flanked with restriction sites and SerGlyAlaGly linker was synthesized (5'ACACAGGATCCTCACTAGGTAGGGTGCTGGACG GTGACCGGACGCGTTGGGGTGGTGGGGCCT CTGGGGCCGGATCCCACCA). (SEQ.ID.NO.:26) Double strand DNA fragment was synthesized by using DNA extension reaction and short complementary oligo. Further, the SEQ. ID. NO.:4 encoding DNA was restricted by Xba I and cloned in open reading frame of mEPO into pCMV/EPO vector. Structure of SEQ. ID. NO.:4-EPO fusion protein was confirmed by DNA sequencing.

Example 13

Conjugation of Paclitaxel Prodrug with Peptide SEQ. ID. NO.:1

Paclitaxel was esterified using maleimidepropionic acid to produce paclitaxel-2' maleinidepropionate (step 1). Paclitaxel-2' maleimidepropionate was then conjugated with peptide (SEQ. ID. NO.:1), and produced the product paclitaxel (S-maleimidepropionate)-peptide(SEQ. ID. NO.: 1). The product was purified by HPLC.

Solution of paclitaxel (6 mg, 0.01 mmol) in 0.1 nL dimethylformamide was mixed with maleimidepropionic acid (2.5 mg) solution in 0.1 mL dimethylformamide, and dicyclohexylcarbodiimide (3 mg solution in 0.1 mL dimethylformantide). The mixture was stirred for 60 minutes. The mixture was fiactionated using reverse phase HPLC with water-acetonitrile gradient (1% per minute, starting from 10% acetonitrile). The fractions containing the product paclitaxel-2' maleimidepropionate were identified by MS (m/z 1003.3).

Paclitaxel-2' maleimidepropionate (1 mg dissolved in 0.1 mL dimethylformamide) was mixed with peptide SEQ. ID. NO.:1 (2 mg dissolved in 0.02 mL DMF), and was stirred for 18 hrs. Then the mixture was diluted with 2 mL water and freezedried. The remaining material was purified with using reverse phase HPLC with water—acetonitrile gradient (1% per minute, starting from 10% acetonitrile). The fractions containing the product paclitaxel-(S-maleimidepropionate)-peptide (SEQ. ID. NO.:1)) were identified by MS (m/z 1240 double charged).

Example 14

Conjugation of Doxorubicin Prodrug with Peptide SEQ. ID. NO.:1

Leucyl-doxorubicin was modified using the heterobiftnctional linker maleimidepropionic acid N-hydroxysuccinimide ester, and gave the produced maleimidepropionyl-leucyl-doxorubicin (step 1). The conjugate peptide (SEQ. ID. NO.: 1)-(S-maleimidepropionylleucyl-doxorubicin) was then prepared by reaction of maleimidepropionylleucyl-doxorubicin with peptide SEQ. ID. NO.: 1 (step 2).

A solution of L-leucyl-doxorubicin (6 mg, 0.01 mmol) in 0.1 mL dimethylformamide was mixed with maleimidepropionic acid N-hydroxysuccinimide ester (3 mg) solution in 0.1 mL dimethylformamide, and diisopropylethylamine (0.015 mL of 10% solution in dimethylformamide). The mixture was stirred for 20 minutes. The mixture was fractionated using reverse phase HPLC with water—acetonitrile gradient (1% per minute, starting from 10% acetonitrile). The fractions containing the product maleimidepropionylleucyl-doxorubicin were identified by MS (m/z 807.3).

Maleimidepropionylleucylleucyl-doxorubicin (1 mg dissolved in 0.1 mL dimethylformamide) was mixed with peptide SEQ. ID. NO.:1 (2 mg dissolved in 0.02 mL DMF), and was stirred for 18 hrs. Then the mixture was diluted with 2 mL water and freezedried. The remaining material was purified with using reverse phase HPLC with water—acetonitrile gradient (1% per minute, starting from 10% acetonitrile). The fractions containing the product (pcptide (SEQ. ID. NO.:1)-Leucyl-doxorubicin) were identified by MS (m/z 1141.5 double charged).

SEQUENCE LISTING

| SEQ. ID. NO.: | Sequence |
|---|---|
| 1 | Ac-Cys-Arg-Val-Leu-Asp-Gly-Asp-Arg-Thr-Arg-Trp-Gly-NH$_2$ |
| 2 | Tamra-Ala-Ser-Ala-Arg-Val-Leu-Asp-Gly-Asp-Arg-Thr-Arg-Trp-Gly-NH$_2$ |
| 3 | Tamra-D-Ala-D-Ser-D-Ala-D-Arg-D-Val-D-Leu-D-Asp-Gly-D-Asp-D-Arg--D-Thr-D-Arg-D-Trp-Gly-NH$_2$ |
| 4 | Arg-Val-Leu-Asp-Gly-Asp-Arg-Thr-Arg-Trp-Gly |
| 5 | Tamra-D-Ala-D-Ser-D-Ala-D-Trp-D-Arg-D-Thr-D-Arg-D-Asp-Gly-D-Asp-D-Leu-D-Val-D-Arg-Gly-NH$_2$ |
| 6 | $Y_1$-$Y_2$-X-$Y_3$-X-$Y_4$-X-$Y_5$, |
| 7 | Arg-Val-X-Asp-X-Asp-X-Thr |

Abbreviations
Ac - acetyl,
Fam - fluorescein-5-carbonyl,
Tamra - carboxytetramethylrodamine
$Y_1$ is positively charged amino acid such as Arg or Lys
$Y_2$ is Val, Leu, Ile or Met
$Y_3$ is negatively charged amino acid such as Glu or Asp
$Y_4$ is negatively charged amino acid such as of Glu or Asp
$Y_5$ is Thr or Ser
X is any amino acid The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A polypeptide comprising an amino acid sequence of the formula $Y_1$-$Y_2$-$X_3$-$Y_4$-$X_5$-$Y_6$-$X_7$-$Y_8$
where $Y_1$ is a positively charged amino acid selected from the group consisting of Arg and Lys $Y_2$ is Val, Leu, Ile or Met $X_3$ is a natural alpha-amino acid $Y_4$ is a negatively charged amino acid selected from the group consisting of Glu and Asp $X_5$ is natural alpha-amino acid $Y_6$ is a negatively charged amino acid selected from the group consisting of Glu and Asp $X_7$ is natural alpha-amino acid $Y_8$ is Thr or Ser wherein said polypeptide crosses the blood brain barrier or the gastrointestinal barrier.

2. The polypeptide of claim 1, wherein said polypeptide comprises the amino acid sequence of SEQ. ID. NO.:1.

3. The polypeptide according to claim 1, wherein said polypeptide comprises the amino acid sequence of SEQ. ID. NO.:2.

4. The polypeptide according to claim 1, wherein said polypeptide comprises the amino acid sequence of SEQ. ID. NO.:4.

5. A pharmaceutical composition comprising a polypeptide of claim 1, and a biological agent.

6. The pharmaceutical composition of claim 5 wherein said polypeptide comprises the amino acid sequence of SEQ. ID. NO.:4.

7. The composition of claim 5 further comprising a carrier.

8. The composition polypoptido of claim 5 further comprising a biological agent and a carrier.

9. A composition comprising the polypeptide of claim 1, with a therapeutic agent.

10. A polypeptide comprising a sequence selected from the group consisting of SEQ ID NO: 1, 2, 4, or 7.

11. The polypeptide according to claim 10, wherein said polypeptide comprises the amino acid sequence of SEQ. ID. NO.:7.

12. The polypeptide of claim 10 comprising the sequence of SEQ ID NO: 1.

13. The polypeptide of claim 10 comprising the sequence of SEQ ID NO.: 4.

14. The polypeptide of claim 10 comprising the sequence of SEQ ID NO: 2.

15. A pharmaceutical composition comprising a polypeptide containing the sequence of SEQ ID NO: 1, 2, 4 or 7 and a biological agent.

16. The pharmaceutical composition of claim 15 furthe comprising a carrier.

17. The pharmaceutical composition of claim 15 comprising said polypeptide and a therapeutic agent.

* * * * *

SEQUENCE LISTING

<160> NUMBER OF SEQ ID NOS: 26

<210> SEQ ID NO 1
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (12)
<223> OTHER INFORMATION: AMIDATION
<223> OTHER INFORMATION: Description of Artificial Sequence: synthetic
      chemical peptide synthesis and biosynthetic
      including use of E. Coli

<400> SEQUENCE: 1

Cys Arg Val Leu Asp Gly Asp Arg Thr Arg Trp Gly
 1               5                  10

<210> SEQ ID NO 2
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: carboxytetramethylrodamine;
<221> NAME/KEY: MOD_RES
<222> LOCATION: (14)
<223> OTHER INFORMATION: AMIDATION
<223> OTHER INFORMATION: Description of Artificial Sequence: synthetic
      chemical peptide synthesis and biosynthetic
      including use of E. Coli

<400> SEQUENCE: 2

Ala Ser Ala Arg Val Leu Asp Gly Asp Arg Thr Arg Trp Gly
 1               5                  10

<210> SEQ ID NO 3
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: carboxytetramethylrodamine;
<221> NAME/KEY: MOD_RES
<222> LOCATION: (14)
<223> OTHER INFORMATION: AMIDATION
<223> OTHER INFORMATION: Description of Artificial Sequence: synthetic
      chemical peptide synthesis and biosynthetic
      including use of E. Coli

<400> SEQUENCE: 3

Ala Ser Ala Arg Val Leu Asp Gly Asp Arg Thr Arg Trp Gly
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: synthetic
      chemical peptide synthesis and biosynthetic
      including use of E. Coli

<400> SEQUENCE: 4

Arg Val Leu Asp Gly Asp Arg Thr Arg Trp Gly
 1               5                   10

<210> SEQ ID NO 5
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: carboxytetramethylrodamine;
<221> NAME/KEY: MOD_RES
<222> LOCATION: (14)
<223> OTHER INFORMATION: AMIDATION
<223> OTHER INFORMATION: Description of Artificial Sequence: synthetic
      chemical peptide synthesis and biosynthetic
      including use of E. Coli

<400> SEQUENCE: 5

Ala Ser Ala Trp Arg Thr Arg Asp Gly Asp Leu Val Arg Gly
 1               5                   10

<210> SEQ ID NO 6
<211> LENGTH: 8
<212> TYPE: PRT
<213> ORGANISM: Artificial Sequence
<220> FEATURE:
<221> NAME/KEY: SITE
<222> LOCATION: (1)
<223> OTHER INFORMATION: positively charged amino acid such as Arg or
      Lys
<221> NAME/KEY: SITE
<222> LOCATION: (2)
<223> OTHER INFORMATION: is Val, Leu, Ile or Met
<221> NAME/KEY: SITE
<222> LOCATION: (3)
<223> OTHER INFORMATION: is any amino acid
<221> NAME/KEY: SITE
<222> LOCATION: (4)
<223> OTHER INFORMATION: negatively charged amino acid such as Glu or
      Asp
<221> NAME/KEY: SITE
<222> LOCATION: (5)
<223> OTHER INFORMATION: is any amino acid
<221> NAME/KEY: SITE
<222> LOCATION: (6)
<223> OTHER INFORMATION: negatively charged amino acid such as Glu or
      Asp
<221> NAME/KEY: SITE
<222> LOCATION: (7)
<223> OTHER INFORMATION: is any amino acid
<221> NAME/KEY: SITE
<222> LOCATION: (8)
<223> OTHER INFORMATION: is Thr or Ser
<223> OTHER INFORMATION: Description of Artificial Sequence: synthetic
      chemical peptide synthesis and biosynthetic
      including use of E. Coli

<400> SEQUENCE: 6

Xaa Xaa Xaa Xaa Xaa Xaa Xaa Xaa
 1               5

<210> SEQ ID NO 7
<211> LENGTH: 8
<212> TYPE: PRT
<213> ORGANISM: Artificial Sequence
<220> FEATURE:
<221> NAME/KEY: SITE
<222> LOCATION: (3)
<223> OTHER INFORMATION: is any amino acid
<221> NAME/KEY: SITE

```
<222> LOCATION: (5)
<223> OTHER INFORMATION: is any amino acid
<221> NAME/KEY: SITE
<222> LOCATION: (7)
<223> OTHER INFORMATION: is any amino acid
<223> OTHER INFORMATION: Description of Artificial Sequence: synthetic
      chemical peptide synthesis and biosynthetic
      including use of E. Coli

<400> SEQUENCE: 7

Arg Val Xaa Asp Xaa Asp Xaa Thr
 1               5

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence: nucleotide

<400> SEQUENCE: 8
gggccggtag ggtgctggac ggtgaccgga cgcgttgggg tggtggcgct tctg      54

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: nucleotide

<400> SEQUENCE: 9
aagcgccacc                                                        10

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: nucleotide

<400> SEQUENCE: 10
accggccccg t                                                      11

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence mutated
      sequence ID 4

<400> SEQUENCE: 11

Ala Val Leu Asp Gly Asp Arg Thr Arg Trp Gly
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 12

Arg Ala Leu Asp Gly Asp Arg Thr Arg Trp Gly
 1               5                  10
```

```
<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 13

Arg Val Ala Asp Gly Asp Arg Thr Arg Trp Gly
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 14

Arg Val Leu Ala Gly Asp Arg Thr Arg Trp Gly
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 15

Arg Val Leu Asp Ala Asp Arg Thr Arg Trp Gly
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 16

Arg Val Leu Asp Gly Ala Arg Thr Arg Trp Gly
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 17

Arg Val Leu Asp Gly Asp Ala Thr Arg Trp Gly
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 18
```

```
Arg Val Leu Asp Gly Asp Arg Ala Arg Trp Gly
 1               5                  10
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 19

```
Arg Val Leu Asp Gly Asp Arg Thr Ala Trp Gly
 1               5                  10
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 20

```
Arg Val Leu Asp Gly Asp Arg Thr Arg Ala Gly
 1               5                  10
```

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 21

```
Arg Val Leu Asp Gly Asp Arg Thr Arg Trp Ala
 1               5                  10
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 22

```
Arg Val Leu Ala Gly Ala Arg Thr Arg Trp Gly
 1               5                  10
```

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: mutated
      sequence ID 4

<400> SEQUENCE: 23

```
Arg Val Leu Asp Gly Asp Ala Thr Ala Trp Gly
 1               5                  10
```

<210> SEQ ID NO 24
<211> LENGTH: 29
<212> TYPE: DNA
<213> ORGANISM: Artificial Sequence

```
<220> FEATURE:
<223> OTHER INFORMATION: Description of Artificial Sequence: sense
      primer

<400> SEQUENCE: 24
ataacaagct tggcgcggag atgggggtg                                    29

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: antisense
      primer

<400> SEQUENCE: 25
ataactctag aacggtggca gcagcatgtc ac                                32

<210> SEQ ID NO 26
<211> LENGTH: 82
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26
acacaggatc ctcactaggt agggtgctgg acggtgaccg gacgcgttgg ggtggtgggg   60
cctctggggc cggatcccac ca                                           82
```